US012780781B2

(12) United States Patent
Wall et al.

(10) Patent No.: US 12,780,781 B2
(45) Date of Patent: Nov. 3, 2026

(54) METHODS OF MAKING DEUTERIUM-ENRICHED N-ACETYLCYSTEINE AMIDE (d-NACA) AND (2R,2R)-3,3-DISULFANEDIYL BIS(2-ACETAMIDOPROPANAMIDE) (diNACA) AND USING d-NACA AND diNACA TO TREAT DISEASES INVOLVING OXIDATIVE STRESS

(71) Applicant: Nacuity Pharmaceuticals, Inc., Fort Worth, TX (US)

(72) Inventors: G. Michael Wall, Fort Worth, TX (US); Neil Beare, Wellington (NZ); Cory A. Black, Wellington (NZ)

(73) Assignee: NACUITY PHARMACEUTICALS, INC., Fort Worth, TX (US)

( * ) Notice: Subject to any disclaimer, the term of this patent is extended or adjusted under 35 U.S.C. 154(b) by 457 days.

(21) Appl. No.: 18/347,896

(22) Filed: Jul. 6, 2023

(65) Prior Publication Data

US 2023/0373913 A1 Nov. 23, 2023

Related U.S. Application Data

(60) Continuation-in-part of application No. 16/928,927, filed on Jul. 14, 2020, now Pat. No. 11,753,370, which is a division of application No. 16/180,984, filed on Nov. 5, 2018, now abandoned.

(60) Provisional application No. 62/587,246, filed on Nov. 16, 2017, provisional application No. 62/583,984, filed on Nov. 9, 2017.

(51) Int. Cl.

| | |
|---|---|
| ***C07C 323/41*** | (2006.01) |
| ***A61K 9/00*** | (2006.01) |
| ***A61K 9/08*** | (2006.01) |
| ***A61K 31/00*** | (2006.01) |
| ***A61K 31/185*** | (2006.01) |
| ***A61K 47/10*** | (2017.01) |
| ***A61P 27/02*** | (2006.01) |
| ***C07C 319/12*** | (2006.01) |
| ***C07C 319/24*** | (2006.01) |
| ***C07C 319/28*** | (2006.01) |
| ***C07D 277/12*** | (2006.01) |

(52) U.S. Cl.

CPC .......... *C07C 323/41* (2013.01); *A61K 9/0048* (2013.01); *A61K 9/08* (2013.01); *A61K 31/00* (2013.01); *A61K 31/185* (2013.01); *A61K 47/10* (2013.01); *A61P 27/02* (2018.01); *C07C 319/12* (2013.01); *C07C 319/24* (2013.01); *C07C 319/28* (2013.01); *C07D 277/12* (2013.01); *C07B 2200/05* (2013.01); *C07B 2200/07* (2013.01)

(58) Field of Classification Search

CPC ...... C07C 323/41; A61P 27/02; A61K 9/0048
See application file for complete search history.

(56) References Cited

U.S. PATENT DOCUMENTS

| | | | |
|---|---|---|---|
| 3,340,147 | A | 9/1967 | Alexander |
| 5,874,468 | A | 2/1999 | Atlas |
| 6,420,429 | B1 | 7/2002 | Atlas |
| 8,354,449 | B2 | 1/2013 | Goldstein |
| 8,937,099 | B2 | 1/2015 | Goldstein |
| 8,993,627 | B2 | 3/2015 | Goldstein |
| 9,216,162 | B2 | 12/2015 | Goldstein |
| 9,763,902 | B2 | 9/2017 | Warner |
| 9,889,103 | B2 | 2/2018 | Warner |
| 10,869,846 | B2 | 12/2020 | Goldstein |

(Continued)

FOREIGN PATENT DOCUMENTS

| | | |
|---|---|---|
| CA | 3078680 A1 | 5/2019 |
| CA | 3079196 | 5/2021 |

(Continued)

OTHER PUBLICATIONS

MedChem News, Deuterium Medicinal Chemistry: A New Approach to Drug Discovery and Development, May 2014, pp. 8-22 (Year: 2014).*

Hsu, et al. "Feasibility of corneal drug delivery of cysteamine using vitamin E modified silicone hydrogel contact lenses" European Journal of Pharn1aceutics and Biopharn1aceutics 85 (2013) 531-540.

Intellectual Property India, First Examination Report for Indian Appl. No. 201917036550 dated Sep. 22, 2021, 7 pp.

Isokawa, et al., Analytical methods involving separation techniques for determination of low-molecular-weight biothiols in human plasma and blood. J Chrom B, 964 (2014) 103-115.

(Continued)

*Primary Examiner* — Sarah Pihonak
*Assistant Examiner* — Mikhail O'Donnel Robinson
(74) *Attorney, Agent, or Firm* — Edwin S. Flores; Daniel J. Chalker; Chalker Flores, LLP

(57) ABSTRACT

The present invention includes pharmaceutical composition comprising (2R,2R')-3,3'-disulfanediyl bis(2-acetamidopropanamide) (diNACA), deuterated NACA-$d_3$, deuterated di-NACA-$d_6$, combinations thereof, or a physiologically acceptable salt thereof, having a deuterium enrichment above the natural abundance of deuterium, and derivatives or solids thereof, and methods of using diNACA, NACA-$d_3$, di-NACA-$d_6$, or combinations thereof, to treat eye diseases and other diseases associated with oxidative damage including, e.g., antivenom, beta-thallassemia, cataract, chronic obstructive pulmonary disease, macular degeneration, contrast-induced nephropathy, asthma, lung contusion, methamphetamine-induced oxidative stress, multiple sclerosis, Parkinson's disease, platelet apoptosis, Tardive dyskinesia, Alzheimer disease, HIV-1-associated dementia, mitochondrial diseases, myocardial myopathy, neurodegenerative diseases, pulmonary fibrosis, skin pigmentation, skin in need of rejuvenation, antimicrobial infection, Friedreich's ataxia.

4 Claims, 13 Drawing Sheets

(56) References Cited

U.S. PATENT DOCUMENTS

| | | | |
|---|---|---|---|
| 11,052,018 | B2 | 7/2021 | Molnar |
| 11,092,017 | B2 | 8/2021 | Propheter-Hinckley |
| 2003/0027745 | A1 | 2/2003 | Repine |
| 2005/0112572 | A1 | 5/2005 | Pincemail |
| 2009/0234011 | A1 | 9/2009 | Goldstein |
| 2012/0142550 | A1 | 6/2012 | Zehnder |
| 2012/0150029 | A1 | 6/2012 | Debuc |
| 2013/0303436 | A1 | 11/2013 | Wilson |
| 2015/0164830 | A1 | 6/2015 | Goldstein |
| 2017/0020914 | A1 | 1/2017 | Castro Feo |
| 2017/0333375 | A1 | 11/2017 | Campochiaro |
| 2017/0370945 | A1 | 12/2017 | Campochiaro |
| 2019/0135741 | A1 | 5/2019 | Wall |
| 2020/0281944 | A1 | 9/2020 | Piraee |

FOREIGN PATENT DOCUMENTS

| | | | |
|---|---|---|---|
| CN | 108618993 | A | 10/2018 |
| EP | 1975621 | A4 | 2/2009 |
| GB | 1114369 | A | 5/1968 |
| JP | 2008538586 | A5 | 7/2009 |
| JP | 202023549 | | 2/2020 |
| WO | WO-9118594 | A * | 12/1991 |
| WO | 2003016527 | A3 | 12/2003 |
| WO | 2004012652 | A3 | 4/2004 |
| WO | 2004028536 | A1 | 4/2004 |
| WO | 2006116353 | A2 | 11/2006 |
| WO | 2010048716 | A1 | 5/2010 |
| WO | 2011044230 | A2 | 4/2011 |
| WO | 2013138744 | A1 | 9/2013 |
| WO | 2013163545 | A1 | 10/2013 |
| WO | 2014025792 | A1 | 2/2014 |
| WO | 2014100361 | A1 | 6/2014 |
| WO | 2015148880 | A1 | 10/2015 |
| WO | 2016073931 | A1 | 5/2016 |
| WO | 2016073829 | A9 | 6/2016 |
| WO | 2017161318 | A1 | 9/2017 |
| WO | 2019060623 | A1 | 3/2019 |
| WO | 2019060634 | A1 | 3/2019 |
| WO | 2019060704 | A1 | 3/2019 |
| WO | 2019094383 | A1 | 5/2019 |
| WO | 2019097434 | A1 | 5/2019 |
| WO | 2019103915 | A1 | 5/2019 |
| WO | 2020102810 | A1 | 5/2020 |
| WO | 2020146660 | A1 | 7/2020 |
| WO | 2020146666 | A1 | 7/2020 |
| WO | 2020146674 | A1 | 7/2020 |

OTHER PUBLICATIONS

Jastrzęebska, et al., "N-acetylcysteine amide (AD4) reduces cocaine-induced reinstatement." Psychopharmacology 2016;33:3437-3448.

Jones, "Extracellular Redox State: Refining the Definition of Oxidative Stress in Aging," Rejuvenation Research (2006), 9(2):169-181.

Kahns, et al., "Prodrugs as drug delivery systems. 107. Synthesis and chemical and enzymatic hydrolysis kinetics of various mono- and diester prodrug of N-acetylcysteine." Int J Pharm (1990), 62:193-205.

Katz, et al., Cerebrospinal fluid concentrations of N-acetylcysteine after oral administration in Parkinson's disease. Parkinsonism and Related Disorders, 21 (2015) 500-503.

Kelly, "Clinical applications of N-acetylcysteine." Altern Med Rev J Clin Ther. (1998), 3(2):114-27.

Kim, et al., "N-Acetylcysteine increases corneal cell survival in a mouse model of Fuchs endothelial corneal dystrophy," Experimental Eye Research (2014), 127:20-25.

Komeima, et al., "Antioxidants reduce cone cell death in a model of retinitis pigmentosa." PNAS, (2006), 103 (30):11300-11305.

Komeina, et al., "Antioxidants slow photoreceptor cell death in mouse models of retinitis pigmentosa." J Cell Physiol. (2007), 213(3):809-15.

Komeina, et al., "Blockade of neuronal nitric oxide synthase reduces cone cell death in a model of retinitis pigmentosa." Free Radic Biol Med, (2008), 45(6):905-12.

Kunisada, et al. "CXCL1 Inhibition Regulates UVB-Induced Skin Inflammation and Tumorigenesis in Xpa-Deficient Mice" Journal of Investigative Dermatology (2017), 137, 1975-1983.

Kusmierek, et al., Ultraviolet derivatization of low-molecular-mass thiols for high performance liquid chromatography and capillary electrophoresis analysis, J Chrom B, 879 (2011) 1290-1307.

Grinberg, et al., "N-acetylcysteine amide, a novel cell-permeating thiol, restores cellular glutathione and protects human red blood cells from oxidative stress," Free Radical Biol Med. (2005) ;38(1):136-145.

Lee, et al., "N-Acetylcysteine Promotes Long-Term Survival of Cones in a Model of Retinitis Pigmentosa," J Cell Physiol (2011), 226:1843-1849, published online Nov. 10, 2010.

Levine, R.L., "Carbonyl modified proteins in cellular regulation, aging, and disease" Free Radic Biol Med, 2002. 32(9): p. 790-6.

Li, et al, "A Convenient Synthesis of Amino Acid Methyl Esters", Molecules (2008), 13:1111-1119.

Liu, et al., "A rabbit model to study biochemical damage to the lens after vitrectomy: effects of N-acetylcysteine." Exp Eye Res. 2009;88(6):1165-70.

Lu, et al., "Effects of Different Types of Oxidative Stress in RPE Cells," J Cell Phys (2006), 206(1):119-125.

Maddirala, et al. "Prevention and reversal of selenite-induced cataracts by N-acetylcysteine amide in Wistar rats" BMC Ophthalmology (2017) 17:54.

Maeda, et al., "Important Role of the 3-Mercaptopropionamide Moiety in Glutathione: Promoting Effect on Decomposition of the Adduct of Glutathione with the Oxoammonium Ion of Tempo", J Organic Chem (2005). 70:8338-8343.

Martin, Tellis, "Amides of N-Acylcysteines as Mucolytic Agents", J Med Chem (1967), 10:1172-1176.

Martinez-Fernandez De La Camara, et al., Altered Antioxidant-Oxidant Status in Aqueous Humor and Peripheral Blood of Patents with Retinitis Pigmentosa, PLOS ONE (2013), 8(9):E74223.

Mcmenamim, et al., Simultaneous analysis of multiple aminothiols in human plasma by high performance liquid chromatography with fluorescence detection, J Chrom B, 877 (2009) 3274-3281.

Minozzi, et al., "An Insight into the Radical Thiol/Yne Coupling: The Emergence of Arylalkyne-tagged Suggars for te Direct Photoinduced Glycosylation of Cysteine Containing Peptides", J. Org. Chem, 2011, 76, 450-459.

Miller, WF. "Aerosol therapy in acute and chronic respiratory disease." Arch Intern Med 1973;131:148-155.

Moore, et al., A new LC-MS/MS method for the clinical determination of reduced and oxidized glutathione from whole blood. J Chrom B, 929 (2013) 51-55.

Nakagami, et al. "A novel Nrf2 activator from microbial transformation inhibits radiation-induced dermatitis in mice," Journal of Radiation Research, vol. 57, No. 5, 2016, pp. 567-571.

Nash, et al., "Nebulized and oral thiol derivatives for pulmonary disease in cystic fibrosis." Cochrane Database Syst Rev 2009;(1):CD007168.

New, et al., Evaluation of BEH C18, BEH HILIC, and HSS T3 (C18) Column Chemistries for the UPLC-MS-MS Analysis of Glutathione, Glutathione Disulfide, and Ophthalmic Acid in Mouse Liver and Human Plasma. J Chrom Sci, 46 (2008) 209-214.

Niemeyer, Selective Rod-and Cone-ERG Responses on Retinal Degenerations, Digital Journal of Ophthalmology, 1998, vol. 4, No. 10, 1998.

Nozal, et al., Determination of glutathione, cysteine, and N-acetylcysteine in rabbit eye tissues using high-performance liquid chromatography and post-column derivatization with 5,5'-dithiobis(2-nitrobenzoic acid). J Chrom A, 778 (1997) 347-353.

Offen, et al. "A low molecular weight copper chelator crosses the blood-brain barrier and attentuates experimental autoimmune encephalomyelitis" Journal of Neurochemistry, 2004, 89, 1241-1251.

Park, et al.: "Targeted and Reversible Blood-Retinal Barrier Disruption via Focused Ultrasound and Microbubbles" PLoS ONE (2012), 7(8):e42754.

(56) References Cited

OTHER PUBLICATIONS

Poole, et al., "Mucolytic agents versus placebo for chronic bronchitis or chronic obstructive pulmonary disease." Cochrane Database Syst Rev 2015;(7):CD001287).
Reagan-Shaw, et al. "Dose translation from animal to human studies revised" The FASEB Journal, Mar. 2007, vol. 22, (659-661).
Reyes, et al., Neuronal glutathione content and antioxidant capacity can be normalized in situ by N-acetyl cysteine concentrations attained in human cerebrospinal fluid, Neurotherapeutics, 13 (2016) 217-225.
Riley, et al., "Glutathione in the aqueous humor of human and other species." Investigative ophthalmology & visual science, (1980), 9(1):94-96.
Rubin BK. "Aerosol Medications for Treatment of Mucus Clearance Disorders Respiratory care" 2015; 60(6): 825-832.
Šalamon, et al., "Medical and Dietary Uses of N-Acetylcysteine." Antioxidants 2019, 8, 111.
Schimel, et al., "N-Acetylcysteine Amide (NACA) Prevents Retinal Degeneration by Up-Regulating Reduced Glutathione Production and Reversing Lipid Peroxidation." The American Journal of Pathology, (2011), 178 (5):2032-2043.
Sekhon, "Exploiting the Poer of Stereochemistry in Drugs . . . . ", Journal of Modern Medicinal Chemistry, 2013, 10-36.
Shen, et al., "Oxidative damage is a potential cause of cone cell death in retinitis pigmentosa." J Cell Physiol, (2005), 203(3):457-64.
Shen, et al., "Oxidative damage in age-related macular degeneration," Histology and Histopathology (2007), 22(12):1301-1308.
Shintani, et al., "Review and Update: Current treatment trends for Patients with Retinitis Pigmentosa," Optometry (2009), 80:384-401.
Adil, et al. "N-acetylcysteine in dermatology" Indian Journal of Dermatology, Feb. 2018.
Amer, et al., "N-acetylcysteine amide (AD4) attenuates oxidative stress in beta-thalassemia blood cells." Biochimica et Biophysica Acta 1780 (2008) 249-255.
Ates, et al., "Antioxidant and free radical scavenging properties of N-acetylcysteine amide (NACA) and comparison with N-acetylcysteine (NAC)." Free Radic Res. (2008), 42(4):372-7.
Australian Patent Office (ISA), International Search Report and Written Opinion for PCT/US2015/060172 Dated Apr. 13, 2016, 12 pg.
Australian Patent Office (ISA), International Search Report and Written Opinion for PCT/US2018/052065 dated Jan. 10, 2019, 10 pg.
Australian Patent Office (ISA), International Search Report and Written Opinion for PCT/US2018/059446 dated Dec. 31, 2018, 15 pg.
Australian Patent Office (ISA), International Search Report and Written Opinion for PCT/US2018/061357 dated Dec. 18, 2018, 11 pg.
Australian Patent Office (ISA), International Search Report and Written Opinion for PCT/US2020/012968 dated Mar. 13, 2020, 10 pp.
Australian Patent Office (ISA), International Search Report and Written Opinion for PCT/US2020/012975 dated Mar. 13, 2020, 12 pp.
Australian Patent Office (ISA), International Search Report and Written Opinion for PCT/US2020/012983 dated Mar. 13, 2020, 15 pp.
Australian Patent Office, International Search Report and Written Opinion PCT/US2021/014819 dated Mar. 25, 2021, 18 pp.
Australian Patent Office, International Search Report and Written Opinion PCT/US2021/036210 dated Jul. 19, 2021, 12 pp.
Australian Patent Office, Examination Report for Australian Appl. No. 2020227015 dated Sep. 24, 2021, 6 pp.
Babizhayev, et al., Revival of the Lens Transparency with N-Acetylcarnosine.: Current Drug Therapy, 2006:1; 91-116.
Bahat-Stroomza, et al., A novel thiol antioxidant that crosses the blood brain barrier protects dopaminergic neurons in experimental models of Parkinson's disease. European Journal of Neuroscience, 2005; 21: 637-646.
Banerjee, et al., "HIV proteins (gp120 and Tat) and methamphetamine in oxidative stress-induced damage in the brain: Potential role of the thiol antioxidant N-acetylcysteine amide." Free Radic Biol Med. May 15, 2010; 48(10): 1388-1398.
Bean, et al., "Comparative evaluation of antioxidant reactivity within obstructed and control rabbit urinary bladder tissue using FRAP and CUPRAC assays," Molecular and Cellular Biochemistry (2008) 323(1-2):139-142.
Bernardes, et al., "From Disulfide- to Thioether-Linked Glycoproteins" Angewandte Chemie, Supporting Information (2008), S1-S97.
Betteridge, John What is Oxidative Stress Metabolism, vol. 49, No. 2, Feb. 2000, pp. 3-8.
Boone, Kevin "The K-Zone: Biophysical Data Tables", 1994-2006, downloaded from www.kevinboone.com on Mar. 14, 2009.
Buss, et al., "Protein carbonyl measurement by a sensitive ELISA method." Free Radic Biol Med, (1997), 23(3):361-6.
Campochiaro, et al., "Oral N-acetylcysteine improves cone function in retinitis pigmentosa patients in phase I trial." J Clin Invest. 2020 130(3):1527-1541.
Canadian Patent Office, Examination Report for Appl. No. 3,046,363 dated Jun. 6, 2022, 4 pp.
Campochiaro, et al. "Is there Excess Oxidative Stress and Damage in Eyes of Patients with Retinitis Pigmentosa" Antioxidants Redox Signaling, (2015) 23(7):643-648.
Campochiaro, et al. "The Mechanism of Cone Cell Death in Retinitis Pigmentosa", Progress in Retinal and Eye Research (2018), 62:24-37.
Carey, et al., "In vivo inhibition of I-buthionine-(S, R)-sulfoximine-induced cataracts by a novel antioxidant, N-acetylcysteine amide." Free Radical Biol Med. 2011;15.
Carey, et al. "N-acetyl-L-cysteine amide protects retinal pigment epithelium against methamphetamine-induced oxidative stress" Journal of Biophysical Chemistry, vol. 3, No. 2, 101-110 (2012).
Carroll, et al., "Simultaneous quantitation of oxidized and reduced glutathione via LC-MS/MS: An insight into the redox state of hematopoietic stem cells." Free Radical Biology and Medicine, 97 (2016) 85-94.
Celma, et al., "Determination of N-acetylcysteine in human plasma by liquid chromatography coupled to tandem mass spectrometry." J Chrom A, 870 (2000) 13-22.
Chastain, et al. "Distribution of topical ocular nepafenac and its active metabolite amfenac to the posterior segment of the eye." Exp Eye Res (2016), 145:58-67.
Davies, et al., "Measurements of protein carbonyls, ortho- and meta-tyrosine and oxidative phosphorylation complex activity in mitochondria from young and old rats." Free Radic Biol Med, (2001), 31(2):181-90.
Demirel, et al. "The preventive effect of N-acetylcysteine on radiation-induced dermatitis in a rat model" Journal of Buon, 15:577-582, 2010.
Devries, et al. "N-acetyl-l-cysteine." J Cell Biochem Suppl (1993), 17F:270-277.
Dietz, et al., "Photochemical Reduction of 5-Bromouracil by Cysteine Derivatives and Coupling of 5-Bromouracil to Cystine Derivatives," Photochemistry and Photobiology (1989), 49(2):121-129.
Dietzsch, et al., "Cystic fibrosis: comparison of two mucolytic drugs for inhalation treatment (acetylcysteine and arginine hydrochloride)." Pediatrics 1975;55:96-100.
Dong, et al., "Compared with N-acetylcysteine (NAC), N-Acetylcysteine Amid (NACA) Provides Increased Protein of Cone Function in a Model of Retinitis Pigmentosa." Investigative Ophthalmology Visual Science, (2014), 55:1-2. (Abstract).
Ehre, et al. An Improved Inhaled Mucolytic to Treat Airway Muco-obstructive Diseases. Am J Respir Crit Care Med. Jan. 15, 2019;199(2):171-180. doi: 10.1164/rccm.201802-02450C.
Ercal, et al., "Effects of a thiol antioxidant in various cataract models," Acta Ophthalmologica (2016), 94:S256 (Abstract).

(56) References Cited

OTHER PUBLICATIONS

Ercal, et al., High-performance liquid chromatography assay for N-acetylcysteine in biological samples following derivatization with N-(1-pyrenyl)maleimide. J Chrom B, 685 (1996) 329-334.
European Patent Office, Extended European Search Report for 15770142.6 dated Oct. 20, 2017.
European Patent Office, Extended European Search Report for EP 15857309.7 dated May 23, 2018.
European Patent Office, Extended European Search Report for 15858590.1 dated May 2, 2018.
European Patent Office, Extended European Search Report for EP 18876329.6 dated Oct. 29, 2019.
European Patent Office, Extended European Search Report for EP 18882212.6 dated Jul. 6, 2021, 8 pp.
European Patent Office, Extended European Search Report for EP 20738980.0 dated Jan. 28, 2022, 9 pp.
Eye Health—No Translation Available (In Japanese).
Giustarini, et al., Pitfalls in the analysis of the physiological antioxidant glutathione (GSH) and its disulfide (GSSG) in biological samples: an elephant in the room. J Chrom B., 1019 (2016) 21-28.
Han, et al., "Efficacy of nebulized acetylcysteine for relieving symptoms and reducing usage of expectorants in patients with radiation pneumonitis." Thoracic Cancer 2018; 1-6. doi: 10.1111/1759-7714.12938.
Hong, et al. "Effect of High-Dose Intravenous N-acetylcysteine on the Concentration of Plasma Sulfur-Containing Amino Acids", The Korean Journal of Internal Medicine: 20:217-223, 2005.
Heymann, et al., "The preparation and Some Biological Properties of the Asperagine Analog L-2@-Amino-2-carboxyethanesulfonamide," J Am Chem Soc (1959), 81(19):5125-5128.
Sunitha, et al., N-acetylcysteine amide: a derivative to fulfull the promises of N-acetylcysteine. Free Radic Res, 47 (2013) 357-367.
Tam, et al., "Nebulized and oral thiol derivatives for pulmonary disease in cystic fibrosis." Cochrane Database Syst Rev 2013;(7):CD007168.
Tarrant et al. "Mucoactive agents for adults with acute lung conditions: A systematic review." Heart Lung (2019) 48(2):141-147.
Tobwala et al. "N-acetylcysteine Amide (NACA), a Novel GSH Prodrug: Its Metabolism and Implications in Health", Labrou, 2013, Capter VI. ISBN:978-1-62417-460-5.
Tsai, et al. "Topical TV-Acetylcysteine Accelerates Wound Healing in Vitro and in Vivo via the PKC/Stat3 Pathway" Int. J. Mol. Sci., 2014, 15, 7563-7578.
Tse, et al., "High-dose N-acetylcysteinine in stable COPD: the 1-year, double-blind, randomized, placebo-controlled HIACE study." Chest, (2013). 144(1):106-118.
Tuson, et al., "Overexpression of CERKL, a gene responsible for retinitis pigmentosa in humans, protects cells from apoptosis induced by oxidative stress." Mol Vis. (2009), 15:168-80.
United States Patent Trademark Office (ISA) International Search Report and Written Opinion PCT/US2015/059589 Dated Feb. 2, 2016, 10 pg.
University of Sao Paulo, et al. "N-Acetyl Cysteine for Cystinosis Patients", ClinicalTrials.gov [online], identifier: NCT01614431, Last update posted: Jun. 20, 2012, htps://clinicaltrials.gov/ct2/show/NCT01614431, [retrieved online Jul. 9, 2021].
Usui, et al., "Overexpression of SOD in retina: Need for increase in H202-detoxifying enzyme in same cellular compartment," Free Radical Biology and Medicine (2011 ), 51(7):1347-1354.
Usui, et al., "Increased expression of catalase and superoxide dismutase 2 reduces cone cell death in retinitis pigmentosa." Mol Ther J Am Soc Gene Ther. (2009), 17(5):778-86.
Usui, et al., "NADPH oxidase plays a central role in cone cell death in retinitis pigmentosa." J Neurochem. (2009), 110(3):1028-37.
Wang, et al., "Relationship of protein-glutathione mixed disulfide and thioltransferase in H2O2-induced cataract in cultured pig lens." Exp Eye Res. May 1997;64(5):693-700.
Wang, et al., "Hyperoxia-induced lens damage in rabbit: protective effects of N-acetylcysteine." Mol Vis. 2009;15:2945-52.
Watanabe, et al., "Skin-whitening and skin-condition-improving effects of topical oxidized glutathione: a double-blind and placebo-controlled clinical trial." Clin Cosmetic Inv Dermatol. 2014;7:267-274.
Weng, Bioanalytical liquid chromatography tandem mass spectrometry methods on underivatized silica columns with aqueous/organic mobile phases. J Chrom B, 796 (2003) 209-224.
Wu, et al., "Effects of N-acetylcysteine amide (NACA, a thiol antioxidant on radiation-induced cytotoxicity in Chenese hamster ovary cells," Life Sciences (2008), 82:1122-1130.
Wu, et al., Separation and quantification of N-acetyl-L-cysteine and N-acetyl-cysteine-amide by HPLC with fluorescence detection. Biomed Chromatogr, 20 (2006) 415-422.
Yu, et al., "Intraretinal oxygen levels before and after photoreceptor loss in the RCS rat." Invest Ophthalmol Vis Sci, (2000), 41(12):3999-4006.
Zhang, et al., "Effects of N-acetylcysteine and glutathione ethyl ester drops on streptozotocin-induced diabetic cataract in rats." Mol Vis. 2008;14:862-70.

* cited by examiner

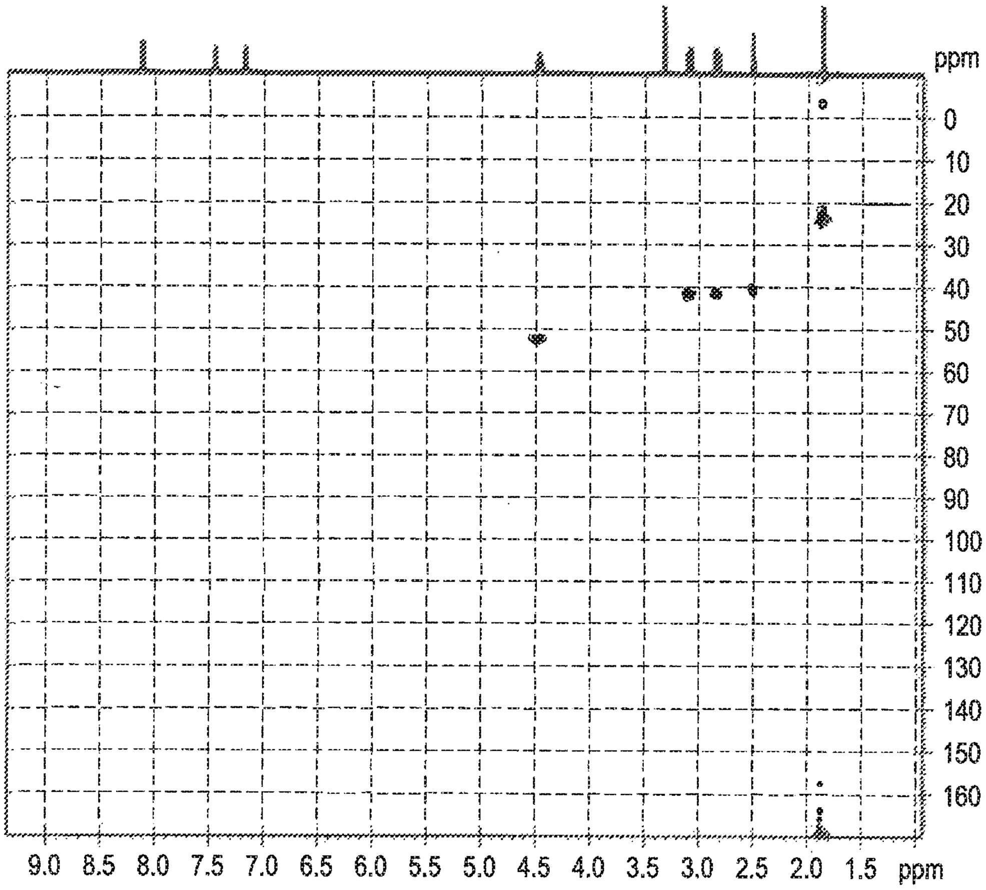

FIG. 3

Current Data Parameters
NAME CS-349-17 HSQC
EXPNO 11
PROCNO 1
F2 - Acquisition Parameters
Date_ 20171006
Time 12.25 h
INSTRUM av500
PROBHD Z107909_0010 (
PULPROG hsqcedetgpsp.3
TD 2048
SOLVENT DMSO
NS 2
DS 64
SWH 4201.681 Hz
FIDRES 4.103204 Hz
AQ 0.2437120 sec
RG 128
DW 119.000 usec
DE 10.00 usec
TE 299.9 K
CNST2 145.0000000
D0 0.00000300 sec
D1 1.46108794 sec
D4 0.00172414 sec
D11 0.03000000 sec
D16 0.00020000 sec
D21 0.00360000 sec
IN0 0.00002210 sec
TDav 1
SFO1 500.1225745 MHz
NUC1 1H
P1 10.00 usec
P2 20.00 usec
P28 0 usec
PLW1 10.00000000 W
SFO2 125.7653344 MHz
NUC2 13C
CPDPRG[2 bi_garp_2pl
P3 8.00 usec
P14 500.00 usec
P31 1895.00 usec PCPD2 70.00 usec
PLW0 0 W
PLW2 30.00000000 W
PLW12 0.39184001 W
PLW30 0.39184001 W
PLW31 1.56729996 W
SPNAM[3] Crp60,0.5,20.1
SPOAL3 0.500
SPOFFS3 0 Hz
SPW3 2.93350005 W
SPNAM[18 Crp60_xfilt.2
SPOAL18 0.500
SPOFFS18 0 Hz
SPW18 0.70662999 W
GPNAM[1] SINE.100
GPZ1 80.00 %
GPNAM[2] SINE.100
GPZ2 20.10 %
P16 1000.00 usec
F1 - Acquisition parameters
TD 256
SFO1 125.7653 MHz
FIDRES 176.753387 Hz
SW 179.894 ppm
FnMODE Echo-Antiecho
F2 - Processing parameters
SI 1024
SF 500.1200000 MHz
WDW QSINE
SSB 2
LB 0 Hz
GB 0
PC 1.40
F1 - Processing parameters
SI 512
MC2 echo-antiecho
SF 125.7552740 MHz
WDW QSINE
SSB 2
LB 0 Hz
GB 0

Current Data Parameters
NAME McPhersonElaine_CS-349-17_061017_1H-2DHSQCed-2DHMBC_av500_OctVII-00
EXPNO 12
PROCNO 1

F2 - Acquisition Parameters
Date_ 20171006
Time 12.40 h
INSTRUM av500
PROBHD Z107909_0010 (
PULPROG hmbcetgp12nd
TD 2048
SOLVENT DMSO
NS 2
DS 32
SWH 4201.681 Hz
FIDRES 4.103204 Hz
AQ 0.2437120 sec
RG 128
DW 119.000 usec
DE 10.00 usec
TE 299.9 K
CNST6 120.0000000
CNST7 160.0000000
CNST13 10.0000000
D0 0.00000300 sec
D1 1.36606097 sec
D6 0.05000000 sec
D16 0.00020000 sec
IN0 0.00001660 sec
SPARSELI 0
TDav 1
SFO1 500.1225745 MHz
NUC1 1H
P1 10.00 usec
P2 20.00 usec
PLW1 10.0000000 W
SFO2 125.7691071 MHz
NUC2 13C
P3 8.00 usec
P24 2000.00 usec
PLW2 30.0000000 W
SPNAM[7] Crp60comp.4
SPOAL7 0.500
SPOFFS7 0 Hz
SPW7 2.93350005 W
GPNAM[1] SINE.100
GPZ1 80.00 %
GPNAM[3] SINE.100
GPZ3 15.00 %
GPNAM[4] SINE.100
GPZ4 -10.00 %
GPNAM[5] SINE.100
GPZ5 -5.00 %
P16 1000.00 usec F1 - Acquisition parameters
TD 128
SFO1 125.7691 MHz
FIDRES 470.632538 Hz
SW 239.490 ppm
FnMODE Echo-Antiecho F2 - Processing parameters
SI 2048
SF 500.1200000 MHz
WDW QSINE
SSB 2
LB 0 Hz
GB 0
PC 1.40

F1 - Processing parameters
SI 1024
MC2 echo-antiecho
SF 125.7552740 MHz
WDW QSINE
SSB 2
LB 0 Hz
GB 0

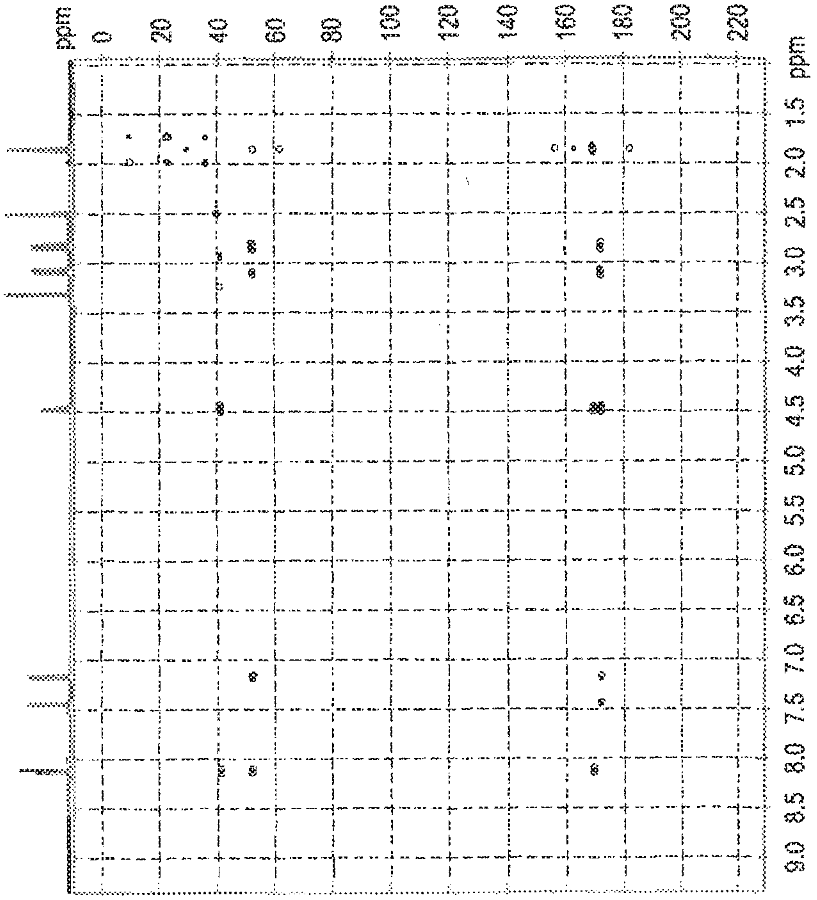

FIG. 4

1719-TTP-13(5)

METHODS OF MAKING DEUTERIUM-ENRICHED N-ACETYLCYSTEINE AMIDE (d-NACA) AND (2R,2R)-3,3-DISULFANEDIYL BIS(2-ACETAMIDOPROPANAMIDE) (diNACA) AND USING d-NACA AND diNACA TO TREAT DISEASES INVOLVING OXIDATIVE STRESS

CROSS-REFERENCE TO RELATED APPLICATIONS

This application is a continuation-in-part of U.S. application Ser. No. 16/928,927, filed Jul. 14, 2020, which is a divisional of U.S. application Ser. No. 16/180,984, filed Nov. 5, 2018, which claims priority to U.S. Provisional Application Ser. No. 62/583,984, filed Nov. 9, 2017 and U.S. Provisional Application Ser. No. 62/587,246, filed Nov. 16, 2018, the entire contents of which are incorporated herein by reference.

STATEMENT OF FEDERALLY FUNDED RESEARCH

None.

TECHNICAL FIELD OF THE INVENTION

The present invention relates in general to the field of making (2R,2R')-3,3'-disulfanediyl bis(2-acetamidopropanamide) (diNACA), (2R,2R')-3,3'-disulfanediyl bis(2-acet($d_3$)amidopropanamide) (diNACA-$d_6$), and N-acetyl ($d_3$) cysteine amide (NACA-$d_3$), pharmaceutical compositions, and methods of making and using NACA-$d_3$, diNACA and diNACA-de to treat diseases associated with oxidative damage including, but not limited to, antivenom, beta-thallassemia, cataract, chronic obstructive pulmonary disease, macular degeneration, contrast-induced nephropathy, asthma, lung contusion, methamphetamine-induced oxidative stress, multiple sclerosis, Parkinson's disease, platelet apoptosis, Tardive dyskinesia, Alzheimer disease, HIV-1-associated dementia, mitochondrial diseases, myocardial myopathy, neurodegenerative diseases, pulmonary fibrosis, retinitis pigmentosa, age-related macular degeneration, skin pigmentation, skin in need of rejuvenation, antimicrobial infection, and/or Friedreich's ataxia.

BACKGROUND OF THE INVENTION

Without limiting the scope of the invention, its background is described in connection with treating oxidative stress in the eye.

One example of an eye disease is Retinitis Pigmentosa (RP), which is the term used for a genetically heterogeneous group of inherited retinal degenerations. In eye disorders caused by oxidative stress an example of an inciting event is a mutation that leads to the death of rod photoreceptors, initially causing night blindness. Rods are the major consumers of oxygen in the retina and the loss of rods causes an increase in the tissue oxygen level in the outer retina. This activates NADPH oxidase causing accumulation of superoxide radicals in the cytosol and also increases their generation in mitochondria of cones. The excess superoxide radicals overwhelm superoxide dismutase 1 and 2 (SOD1 and SOD2) and cause a chain reaction by which other free radicals are generated including some that are even more damaging than superoxide radicals, such as hydroxyl radicals and peroxynitrite. The free radicals attack proteins, lipids, and DNA causing specific modifications that indicate that oxidative damage has occurred. Oxidative damage to lipids results in lipid hydroperoxides that break down to form 4-hydroxynonenal, malondialdehyde (MDA), and acrolein. The most common modification to proteins from oxidative damage is the formation of carbonyl adducts. Measurements of these markers of oxidative damage, such as MDA or the carbonyl adducts, provide a quantitative assessment of the amount of oxidative damage that has occurred in a tissue. These modifications can impair the function of macromolecules and while there are endogenous repair processes, they are overwhelmed by severe oxidative stress resulting in reduced cellular function and eventually apoptosis. After rods are eliminated from the photoreceptor layer, oxidative stress in the outer retina is severe and leads to gradual cone cell death usually starting in the midperiphery where cone density is low and then spreading peripherally and posteriorly (centrally). The posterior spread of cone death results in constriction of the visual field and eventually a central island of vision and its elimination causes blindness.

Currently, there is no approved therapy that stops the evolution of the disease or restores vision. The therapeutic approach is restricted to slowing down the degenerative process by sunlight protection and vitamin A supplementation, treating complications (cataract and macular edema), and helping patients to cope with the social and psychological impact of blindness. Although the Argis II Retinal Prosthesis System was approved by FDA in 2013 as an implanted Humanitarian device (HUD) to treat adults with several RP, it only produces the sensation of light, thereby helping patients identify the location or movement of objects and people; the device is not disease modifying. Based on studies in animal models described below, NACA is able to treat RP in vivo.

As such, there still exists a need for novel compositions and methods for treatment of retinitis pigmentosa.

SUMMARY OF THE INVENTION

As embodied and broadly described herein, an aspect of the present disclosure relates to a method of treating a disease associated with oxidative damage, comprising administering a pharmaceutical composition comprising deuterated (2R,2R')-3,3'-disulfanediyl bis(2-acetamidopropanamide) (di-NACA-$d_6$), deuterated N-acetyl cysteine amide (NACA-$d_3$), diNACA, or combinations thereof, to a patient in need thereof. In one aspect, the disease is an eye disease or disorder. In another aspect, the disease is retinitis pigmentosa, cataracts, age-related macular degeneration, glaucoma, or diabetic retinopathy. In another aspect, the disease is beta-thalassemia, cataracts, chronic obstructive pulmonary disease, macular degeneration, contrast-induced nephropathy, asthma, lung contusion, methamphetamine-induced oxidative stress, multiple sclerosis, Parkinson's disease, platelet apoptosis, Tardive dyskinesia, Alzheimer disease, HIV-1-associated dementia, mitochondrial diseases, myocardial myopathy, neurodegenerative diseases, pulmonary fibrosis, skin pigmentation, skin in need of rejuvenation, antimicrobial infection, or Friedreich's ataxia. In another aspect, the (2R,2R')-3,3'-disulfanediyl bis(2-acetamidopropanamide) (diNACA), NACA-$d_3$, di-NACA-$d_6$, or combinations thereof are used to prevent corneal endothelial cell loss. In another aspect, a dose of the Di-NACA-de is from about 1 mg to 1000 mg, from about 1 mg to about 450 mg, from about 0.1 mg to about 150 mg, from about 1 mg to about 300 mg, from about 10 mg to about 100 mg, from about 0.1 mg to about 50 mg, from about 1 mg to about 50 mg, from about 10 mg to about 50 mg, from about 20 mg to about 30 mg, or from about 1 mg to about 20 mg.

As embodied and broadly described herein, an aspect of the present disclosure relates to a method of making deuterated (2R,2R')-3,3'-disulfanediyl bis(2-acetamidopropanamide) (Di-NACA-$d_6$) comprising the steps of:

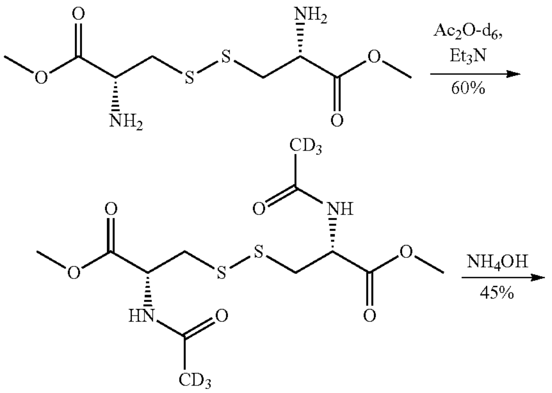

N,N'-Diacetyl-, L-Cystine 1,1'-dimethyl ester-d6

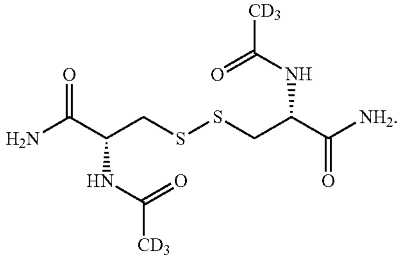

Di-NACA-d6

In one aspect, the method further comprises the step of formulating a pharmaceutical composition by mixing the diNACA-do with a pharmaceutically acceptable adjuvant or additive.

As embodied and broadly described herein, an aspect of the present disclosure relates to A method of treating an eye disease comprising administering a pharmaceutical composition comprising (2R,2R')-3,3'-disulfanediyl bis(2-acetamidopropanamide) (diNACA), NACA-$d_3$, di-NACA-$d_6$, or combinations thereof to a patient in need thereof, wherein the eye disease or disorder is selected from retinitis pigmentosa, cataracts, age-related macular degeneration, glaucoma, or diabetic retinopathy. In one aspect, the diNACA, NACA-$d_3$, di-NACA-$d_6$, or combinations thereof, is at least 98% pure and is formulated for oral, enteral, parenteral, intravenous, subcutaneous, ocular, ocular implant, topical, or other administration. In another aspect, the (2R,2R')-3,3'-disulfanediyl bis(2-acetamidopropanamide) (diNACA), NACA-$d_3$, di-NACA-$d_6$, or combinations thereof are used to prevent corneal endothelial cell loss.

As embodied and broadly described herein, an aspect of the present disclosure relates to a pharmaceutical composition comprising deuterated di-N-acetylcysteine amide-$d_6$ (diNACA-$d_6$), or a physiologically acceptable salt thereof, having a deuterium enrichment above the natural abundance of deuterium; and $D_3$-N-acetyl cysteine amide, or a physiologically acceptable derivative thereof, having a deuterium enrichment above the natural abundance of deuterium. In one aspect, the deuterated di-N-acetylcysteine amide-do has the following formula:

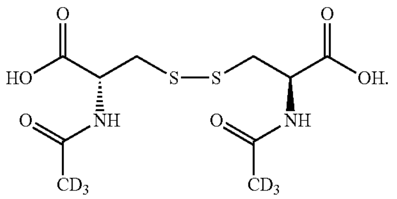 [SMILES: [2H]C([2H])([2H])C(=O)N[C@@H](CSSC[C@H](NC(=O)C([2H])([2H])[2H])C(=O)O)C(=O)O]

In another aspect, the difference in the deuterium enrichment in the $D_6$-positions in the $D_6$-N-acetyl cysteine is about 8 to 10 percentage points. In another aspect, the deuterium enrichment above the natural abundance of deuterium is within a predefined range of 0.02 mol % to 100 mol % deuterium, as determined by NMR spectroscopy in do-dimethyl sulfoxide using a 500 MHz spectrometer. In another aspect, the NACA-$d_3$ is enantiopure (R)-2-acetylamino-3-mercapto-propamide, the NACA-do is enantiopure(S)-2-acetylamino-3-mercapto-propamide, or the NACA-do is a racemic mixture of (R)-2-acetylamino-3-mercapto-propamide and(S)-2-acetylamino-3-mercapto-propamide.

As embodied and broadly described herein, an aspect of the present disclosure relates to a method of making deuterium-enriched di-N-acetylcysteine amide-$d_6$ (di-NACA-$d_6$) comprising the steps of: adding triethylamine to L-Cystine dimethyl ester dihydrochloride in dry acetonitrile at 0° C. under an argon atmosphere; adding acetic anhydride-de and stirring under argon; quenching with deuterium chloride in $D_2O$; extracting with ethyl acetate; washing one or more times with saturated $NaHCO_3$ and brine; drying and filtering in vacuo to give a solid; adding ammonium hydroxide at 0° C. under argon; removing solvent in vacuo by azeotroping one or more times with ethanol; recrystallizing one or more times with water; and drying under vacuum to give a solid.

As embodied and broadly described herein, an aspect of the present disclosure relates to a method of treating a disease associated with oxidative damage, comprising administering a pharmaceutical composition comprising (2R,2R')-3,3'-disulfanediyl bis(2-acetamidopropanamide) (diNACA), NACA-$d_3$, di-NACA-de to a patient in need thereof, wherein the (2R,2R')-3,3'-disulfanediyl bis(2-acetamidopropanamide) (diNACA), NACA-$d_3$, ·25 or di-NACA-$d_6$, or combinations thereof is at least 93% pure. In one aspect, the disease is an eye disease or disorder. In another aspect, the disease is retinitis pigmentosa, age-related macular degeneration, glaucoma, or diabetic retinopathy. In another aspect, the disease is beta-thalassemia, cataracts, chronic obstructive pulmonary disease, macular degeneration, contrast-induced nephropathy, asthma, lung contusion, methamphetamine-induced oxidative stress, multiple sclerosis, Parkinson's disease, platelet apoptosis, Tardive dyskinesia, Alzheimer disease, HIV-1-associated dementia, mitochondrial diseases, myocardial myopathy, neurodegenerative diseases, pulmonary fibrosis, skin pigmentation, skin in need of rejuvenation, antimicrobial infection, or Friedreich's ataxia. In another aspect, 1 dose of the diNACA, NACA-$d_3$, di-NACA-$d_6$, or combinations thereof, is from about 1 mg to 1000 mg, from about 1 mg to about 450 mg, from about 0.1 mg to about 150 mg, from about 1 mg to about 300 mg, from about 10 mg to about 100 mg, from about 0.1 mg to about 50 mg, from about 1 mg to about 50 mg, from about 10 mg to about 50 mg, from about 20 mg to about 30 mg, or from about 1 mg to about 20 mg. In another aspect, the diNACA, NACA-$d_3$, di-NACA-do, or combinations thereof, is at least 98% pure and is formulated for oral, enteral, parenteral, intravenous, subcutaneous, ocular, ocular implant, topical, or other administration.

As embodied and broadly described herein, an aspect of the present disclosure relates to a pharmaceutical composition comprising (2R,2R')-3,3'-disulfanediyl bis(2-acetamidopropanamide) (diNACA) and derivatives or solids thereof. In one aspect, the (2R,2R')-3,3'-disulfanediyl bis(2-acetamidopropanamide) has the following formula:

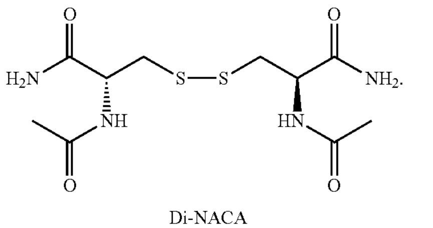

Di-NACA
$C_{10}H_{18}N_4O_4S_2$
Mol WT: 322.40

In another aspect, the (2R,2R')-3,3'-disulfanediyl bis(2-acetamidopropanamide) and derivatives or solids thereof comprises 0.1 mole percent (mol %) to 97 mol % of (2R,2R')-3,3'-disulfanediyl bis(2-acetamidopropanamide). In another aspect, the (2R,2R')-3,3'-disulfanediyl bis(2-acetamidopropanamide) and derivatives or solids thereof comprises 5 mol % to 95 mol % of the (2R,2R')-3,3'-disulfanediyl bis(2-acetamidopropanamide). In another aspect, the (2R,2R')-3,3'-disulfanediyl bis(2-acetamidopropanamide) and derivatives or solids thereof comprises 78 mol % to 95 mol % of (2R,2R')-3,3'-disulfanediyl bis(2-acetamidopropanamide). In another aspect, the (2R,2R')-3,3'-disulfanediyl bis(2-acetamidopropanamide) and derivatives or solids thereof comprises 88 mol % to 92 mol % of (2R,2R')-3,3'-disulfanediyl bis(2-acetamidopropanamide). In another aspect, the (2R,2R')-3,3'-disulfanediyl bis(2-acetamidopropanamide) and derivatives or solids thereof comprises 78 mol % to 82 mol % of (2R,2R')-3,3'-disulfanediyl bis(2-acetamidopropanamide). In another aspect, the (2R,2R')-3,3'-disulfanediyl bis(2-acetamidopropanamide) and derivatives or solids thereof comprises 90 mol % of (2R,2R')-3,3'-disulfanediyl bis(2-acetamidopropanamide) and 10 mol % of (2R,2R')-3,3'-disulfanediyl bis(2-acetamidopropanamide). In another aspect, the (2R,2R')-3,3'-disulfanediyl bis(2-acetamidopropanamide) and derivatives or solids thereof comprises 80 mol % of (2R,2R')-3,3'-disulfanediyl bis(2-acetamidopropanamide) and 20 mol % of (2R,2R')-3,3'-disulfanediyl bis(2-acetamidopropanamide). In another aspect, the (2R,2R')-3,3'-disulfanediyl bis(2-acetamidopropanamide) and derivatives or solids thereof comprises 85 mol % of (2R,2R')-3, (2R,2R')-3,3'-disulfanediyl bis(2-acetamidopropanamide)N-acetyl cysteine amide. In another aspect, the (2R,2R')-3,3'-disulfanediyl bis(2-acetamidopropanamide) and derivatives or solids thereof comprises 70 mol % of (2R,2R')-3,3'-disulfanediyl bis(2-acetamidopropanamide) and 30 mol % of (2R,2R')-3,3'-disulfanediyl bis(2-acetamidopropanamide). In another aspect, the pharmaceutical composition further comprises a pharmaceutically acceptable adjuvant or additive. In another aspect, the diNACA is enantiopure (2R,2R')-3,3'-disulfanediyl bis(2-acetamidopropanamide). In another aspect, the diNACA is enantiopure (2S,2S')-3,3'-disulfanediyl bis (2-acetamidopropanamide). In another aspect, the diNACA is a racemic mixture of (2R,2R')-3,3'-disulfanediyl bis(2-acetamidopropanamide) and (2S,2S')-3,3'-disulfanediyl bis (2-acetamidopropanamide). In another aspect, the diNACA is enantiopure (2R,2R')-3,3'-disulfanediyl bis(2-acetamidopropanamide). In another aspect, the diNACA is enantiopure (2S,2S')-3,3'-disulfanediyl bis(2-acetamidopropanamide). In another aspect, the diNACA is a racemic mixture of (2R,2R')-3,3'-disulfanediyl bis(2-acetamidopropanamide) and (2S,2S')-3,3'-disulfanediyl bis(2-acetamidopropanamide).

In another embodiment, the present invention includes a method of treating a disease associated with oxidative damage, comprising administering a pharmaceutical composition comprising (2R,2R')-3,3'-disulfanediyl bis(2-acetamidopropanamide) (diNACA) to a patient in need thereof. In one aspect, the disease is an eye disease or disorder. In another aspect, the disease is retinitis pigmentosa, age-related macular degeneration, glaucoma, or diabetic retinopathy. In another aspect, the disease is antivenom, beta-thallassemia, cataract, chronic obstructive pulmonary disease, macular degeneration, contrast-induced nephropathy, asthma, lung contusion, methamphetamine-induced oxidative stress, multiple sclerosis, Parkinson's disease, platelet apoptosis, Tardive dyskinesia, Alzheimer disease, HIV-1-associated dementia, mitochondrial diseases, myocardial myopathy, neurodegenerative diseases, pulmonary fibrosis, Friedreich's ataxia.

As embodied and broadly described herein, an aspect of the present disclosure relates to a method of making (2R,2R')-3,3'-disulfanediyl bis(2-acetamidopropanamide) (Di-NACA) comprising the steps of: forming L-Cystine Dimethylester Dihydrochloride from L-cystine by the following reaction:

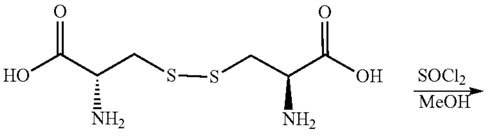

L-Cystine
$C_6H_{12}N_2O_4S_2$
Mol Wt: 240.29

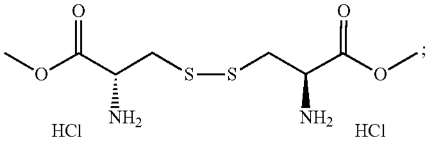

L-Cystine Dimethylester
Dihydrochloride
$C_8H_{16}N_2O_4S_2$ forming Di-NACMe from L-Cystine Dimethylester Dihydrochloride by the following reaction:

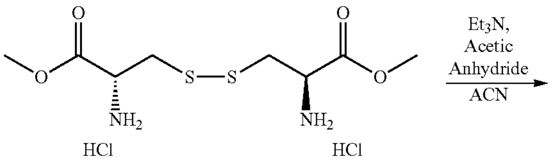

L-Cystine Dimethylester
Dihydrochloride
$C_8H_{16}N_2O_4S_2$
Mol Wt: 341.26

-continued

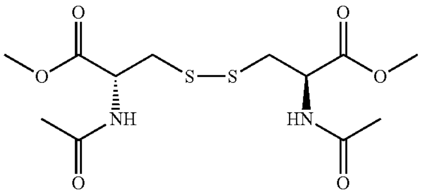

Di—NACMe
$C_{12}H_{20}N_2O_6S_2$
Mol Wt: 352.42

;

generating DiNACA from Di-NACMe by the following reaction:

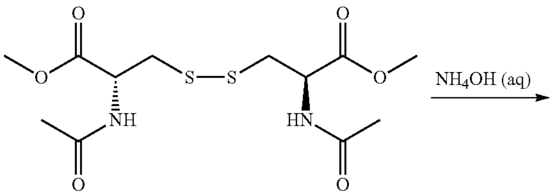

Di-NACMe
$C_{12}H_{20}N_2O_6S_2$
Mol Wt: 352.42

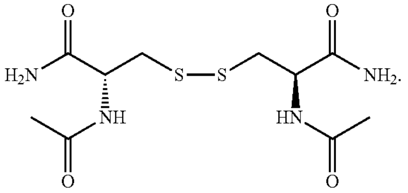

Di-NACA
$C_{10}H_{18}N_4O_4S_2$
Mol Wt: 322.40

In one aspect, the methods further comprises the step of purifying the DiNACA by the following reaction:

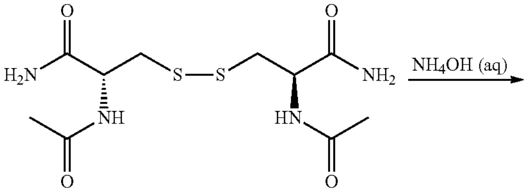

Di—NACA
$C_{10}H_{18}N_4O_4S_2$
Mol Wt: 322.40

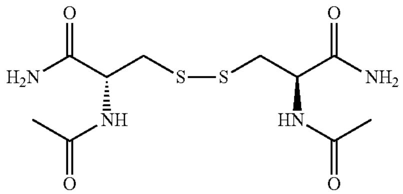

Di—NACA
$C_{10}H_{18}N_4O_4S_2$
Mol Wt: 322.40

.

In another aspect, the purified diNACA comprises 0.1 mol % to 97 mol % of (2R,2R')-3,3'-disulfanediyl bis(2-acetamidopropanamide). In another aspect, the purified diNACA comprises 5 mol % to 95 mol % of the (2R,2R')-3,3'-disulfanediyl bis(2-acetamidopropanamide). In another aspect, the purified diNACA comprises 78 mol % to 95 mol % of (2R,2R')-3,3'-disulfanediyl bis(2-acetamidopropanamide). In another aspect, the purified diNACA comprises 88 mol % to 92 mol % of (2R,2R')-3,3'-disulfanediyl bis(2-acetamidopropanamide). In another aspect, the purified DiNACA comprises 78 mol % to 82 mol % of (2R,2R')-3,3'-disulfanediyl bis(2-acetamidopropanamide). In another aspect, the purified diNACA comprises 90 mol % of (2R,2R')-3,3'-disulfanediyl bis(2-acetamidopropanamide) and 10 mol % of (2R,2R')-3,3'-disulfanediyl bis(2-acetamidopropanamide). In another aspect, the purified diNACA comprises 80 mol % of (2R,2R')-3,3'-disulfanediyl bis(2-acetamidopropanamide) and 20 mol % of (2R,2R')-3,3'-disulfanediyl bis(2-acetamidopropanamide). In another aspect, the purified diNACA comprises 85 mol 1% of (2R,2R')-3, (2R,2R')-3,3'-disulfanediyl bis(2-acetamidopropanamide)N-acetyl cysteine amide. In another aspect, the purified DiNACA comprises 70 mol % of (2R,2R')-3,3'-disulfanediyl bis(2-acetamidopropanamide) and 30 mol % of (2R,2R')-3,3'-disulfanediyl bis(2-acetamidopropanamide). In another aspect, the method further comprises the step of formulating a pharmaceutical composition by mixing the diNACA with a pharmaceutically acceptable adjuvant or additive.

As embodied and broadly described herein, an aspect of the present disclosure relates to a pharmaceutical composition comprising deuterated N-acetylcysteine amide (NACA-$d_3$), or a physiologically acceptable salt thereof, having a deuterium enrichment above the natural abundance of deuterium; and $D_3$-N-acetyl cysteine amide, or a physiologically acceptable derivative thereof, having a deuterium enrichment above the natural abundance of deuterium. In one aspect, the deuterated N-acetylcysteine amide has the following formula:

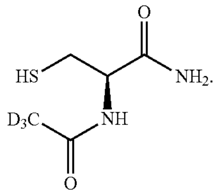 [SMILES: [2H]C([2H])([2H])C(=O)N[C@@H](CS)C(N)=O]

In another aspect, the pharmaceutical composition may comprise 0.1 mole/percent (mol %) to 97 mol % of the $D_3$-N-acetyl cysteine amide. In another aspect, the pharmaceutical composition may comprise 5 mol % to 95 mol % of the $D_3$-N-acetyl cysteine amide. In another aspect, the pharmaceutical composition may comprise 78 mol % to 95 mol % of the $D_3$-N-acetyl cysteine amide. In another aspect, the pharmaceutical composition may comprise 88 mol % to 92 mol % of the $D_3$-N-acetyl cysteine amide. In another aspect, the pharmaceutical composition may comprise 78 mol % to 82 mol % of the $D_3$-N-acetyl cysteine amide.

In another aspect, the pharmaceutical composition may comprise 90 mol % of the $D_3$-N-acetyl cysteine and 10 mol % of the N-acetyl cysteine amide. In another aspect, the pharmaceutical composition may comprise 80 mol % of the $D_3$-N-acetyl cysteine and 20 mol % of the N-acetyl cysteine amide. In another aspect, the pharmaceutical composition may comprise 85 mol % of the $D_3$-N-acetyl cysteine amide and 15 mol % of the N-acetyl cysteine amide. In another aspect, the pharmaceutical composition may comprise 70 mol % of the $D_3$-N-acetyl cysteine amide and 30 mol % of the N-acetyl cysteine amide. In another aspect, the deuterium enrichment in $D_3$-position in the $D_3$-N-acetyl cysteine amide is about 90 mol % to 98 mol %. In another aspect, the difference in the deuterium enrichment in the $D_3$-positions in the $D_3$-N-acetyl cysteine is about 8 to 10 percentage points. In another aspect, the pharmaceutical composition may further comprise a pharmaceutically acceptable adjuvant or additive.

In another aspect, the pharmaceutical composition may comprise deuterium enrichment above the natural abundance of deuterium is within a predefined range of 0.02 mol % to 100 mol % deuterium, as determined by NMR spectroscopy in do-dimethyl sulfoxide using a 500 MHz spectrometer. In another aspect, the NACA-$d_3$ is enantiopure (R)-2-acetylamino-3-mercapto-propamide. In another aspect, the NACA-$d_3$ is enantiopure(S)-2-acetylamino-3-mercapto-propamide. In another aspect, the NACA-$d_3$ is a racemic mixture of (R)-2-acetylamino-3-mercapto-propamide and(S)-2-acetylamino-3-mercapto-propamide.

As embodied and broadly described herein, an aspect of the present disclosure relates to a method of treating a disease associated with oxidative damage, comprising administering a pharmaceutical composition comprising, consisting essentially of, or consisting of: diNACA, NACA-$d_3$, di-NACA-do, or combinations thereof, to a patient in need thereof. In one aspect, the disease is a disease of the eye. In another aspect, the disease is retinitis pigmentosa, age-related macular degeneration, glaucoma, or diabetic retinopathy. In another aspect, the disease is antivenom, beta-thallassemia, cataract, chronic obstructive pulmonary disease, macular degeneration, contrast-induced nephropathy, asthma, lung contusion, methamphetamine-induced oxidative stress, multiple sclerosis, Parkinson's disease, platelet apoptosis, Tardive dyskinesia, Alzheimer disease, HIV-1-associated dementia, mitochondrial diseases, myocardial myopathy, neurodegenerative diseases, pulmonary fibrosis, or Friedreich's ataxia.

As embodied and broadly described herein, an aspect of the present disclosure relates to a method of making deuterium enriched N-acetylcysteine amide (NACA-$d_3$) comprising the steps of:

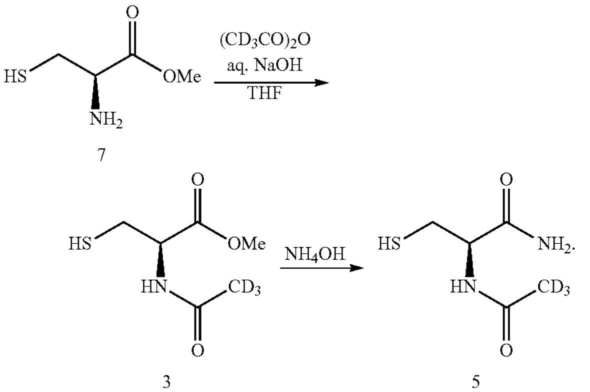

7

3

5

In another embodiment, the present invention includes a method of making deuterium enriched N-acetylcysteine amide (NACA-$d_3$) comprising the steps of:

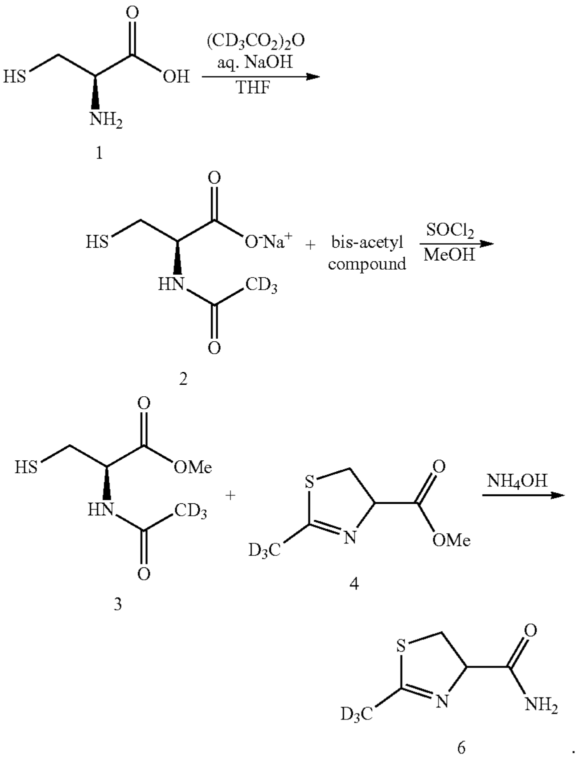

1

2

3

4

6

BRIEF DESCRIPTION OF THE DRAWINGS

For a more complete understanding of the features and advantages of the present invention, reference is now made to the detailed description of the invention along with the accompanying figures and in which:

FIG. 3 shows heteronuclear single quantum correlation spectrum for (2R,2R')-3,3'-disulfanediyl bis(2-acetamidopropanamide) of the present invention.

FIG. 4 shows heteronuclear multiple-bond correlation spectrum for (2R,2R')-3,3'-disulfanediyl bis(2-acetamidopropanamide) of the present invention.

DETAILED DESCRIPTION OF THE INVENTION

Figure 1:
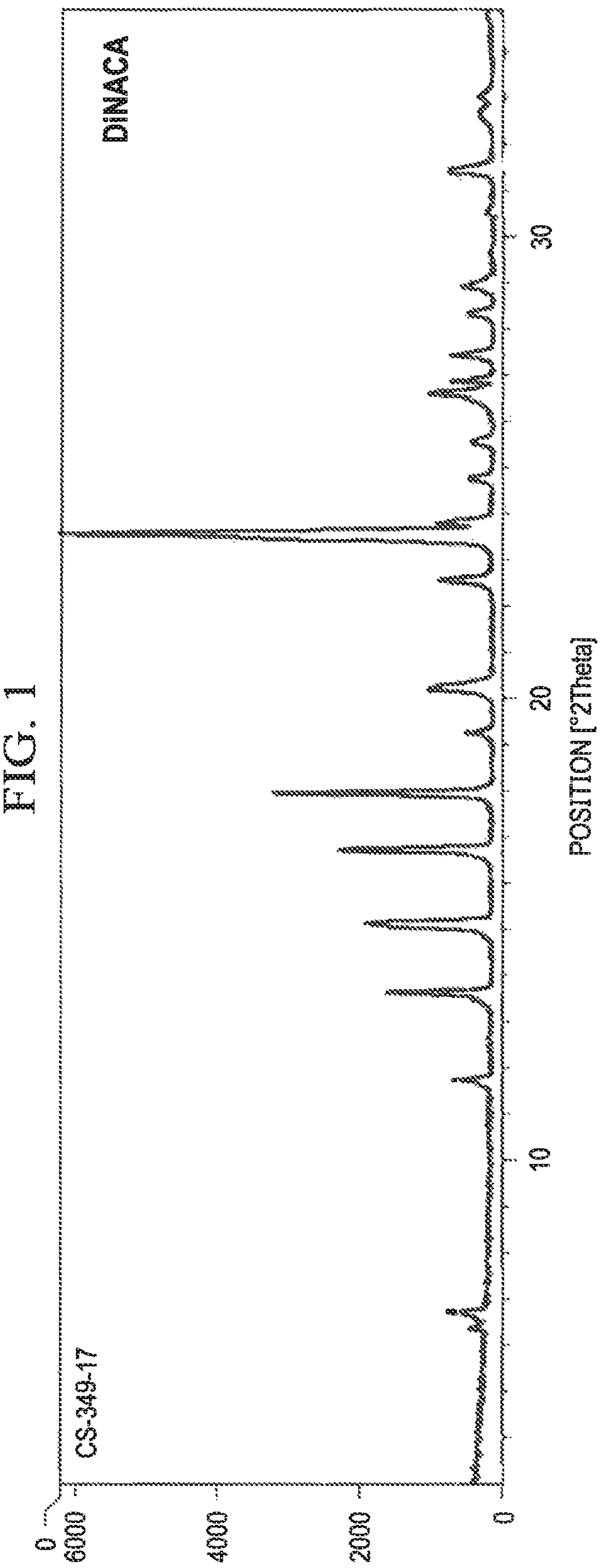
FIG. 1 is an X-Ray Powder Diffractogram for (2R,2R')-3,3'-disulfanediyl bis(2-acetamidopropanamide) of the present invention.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below.

Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

This invention pertains to (2R,2R')-3,3'-disulfanediyl bis (2-acetamidopropanamide), which is also known as diNACA, diNaca, di-NACA, DiNACA, Di-NACA, dimer of NACA, NACA dimer, NACA disulfide, each of which is used interchangeably herein.

This invention pertains to deuterated N-acetylcysteine amide, also known as deuterated NPI-001, deuterated NACA, deuterated AD4, deuterated BB-001, deuterated (R)-2-acetylamino)-3-mercapto-propamide, deuterated N-acetyl-L-cysteinamide, or deuterated acetylcysteine-amide, NACA-$d_3$, di-NACA-do, or combinations thereof,. This invention pertains to deuterated N-acetylcysteine amide, deuterated NPI-001, deuterated NACA, deuterated AD4, deuterated BB-001, deuterated (R)-2-acetylamino-3-mercapto-propamide, deuterated N-acetyl-L-cysteinamide, or deuterated acetylcysteineamide, all of which are used interchangeably.

This invention also pertains to diNACA, NACA-$d_3$, di-NACA-$d_6$, or combinations thereof, treatment of eye diseases associated with oxidative damage, but also other diseases associated with oxidative damage including, but not limited to, antivenom, beta-thallassemia, cataract, chronic obstructive pulmonary disease, macular degeneration, contrast-induced nephropathy, asthma, lung contusion, methamphetamine-induced oxidative stress, multiple sclerosis, Parkinson's disease, platelet apoptosis, Tardive dyskinesia, Alzheimer disease, HIV-1-associated dementia, mitochondrial diseases, myocardial myopathy, neurodegenerative diseases, pulmonary fibrosis, Friedreich's ataxia.

As used herein, the term "deuterium-enriched" refers to the feature that the compound has a quantity of deuterium that is greater than in naturally occurring compounds or synthetic compounds prepared from substrates having the naturally occurring distribution of isotopes. The invention provides deuterium-enriched, deuterated-N-acetyl cysteine amide, pharmaceutical compositions, and methods of treating eye disorders, and other medical disorders using, e.g., an enantiopure or enantio-enriched deuterium-enriched NACA-$d_3$, di-NACA-$d_6$, or combinations thereof. The threshold amount of deuterium enrichment is specified in certain instances in this disclosure, and all percentages given for the amount of deuterium present are mole percentages.

As used herein, the term "effective amount" refers to the amount of a compound sufficient to effect beneficial or desired results. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the eye condition, eye disease, eye disorder, and the like, or ameliorating a symptom thereof.

As used herein, the term "therapeutically effective amount" refers to an amount of a compound of the invention that is effective when administered alone or in combination to treat the desired condition or disorder. A "therapeutically effective amount" includes an amount of the combination of compounds claimed that is effective to treat the desired condition or disorder. The combination of compounds can be additive and is preferably a synergistic combination. Synergy occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower incidence of adverse side effects and/or toxicity, increased efficacy, or some other beneficial effect of the combination compared with the individual components.

Age-related macular degeneration ("AMD") comprises a large group of inherited vision disorders that cause progressive loss of photoreceptor cells of the retina, leading to severe vision impairment and often incurable blindness. The most common form of AMD is a rod-cone dystrophy, in which the first symptom is night blindness, followed by progressive loss in the peripheral visual field in daylight, and eventually leading to blindness after several decades. As a common pathology, rod photoreceptors die early, whereas light-insensitive, morphologically altered cone photoreceptors persist longer.

Diabetic retinopathy (DR), sometimes referred to as diabetic eye disease, in which diabetes mellitus leads to damage to the retina, and is a leading cause of blindness. Typically, DR affects up to 80 percent of diabetic patients. Importantly, the longer a patient has diabetes, the higher the chances of developing diabetic retinopathy. In the United States, diabetic retinopathy accounts for 12% of all new cases of blindness, and is the leading cause of blindness in patients aged 20 to 64.

Glaucoma described several eye diseases that result from damage to the optic nerve leading to loss of vision. Typical symptoms of glaucoma include, e.g., eye pain, blurred vision, mid-dilated pupil, redness of the eye, and nausea. An increase in intraocular pressure is a major risk factor for glaucoma, as are a family history of glaucoma and high blood pressure, however, the etiology of glaucoma is still under investigation.

DiNACA, NACA-$d_3$, di-NACA-$d_6$, or combinations thereof, is typically administered in admixture with suitable pharmaceutical salts, buffers, diluents, extenders, excipients, implants, and/or carriers (collectively referred to herein as a pharmaceutically acceptable carrier or carrier materials) selected based on the intended form of administration and as consistent with conventional pharmaceutical practices.

Depending on the best location for administration, diNACA may be formulated to provide, e.g., maximum and/or consistent dosing for the particular form for oral, rectal, topical (including ophthalmic), inhalation, intranasal, injection (intravenous or intraocular) or parenteral administration. While diNACA, NACA-$d_3$, di-NACA-$d_6$, or combinations thereof, may be administered alone, it will generally be provided in a stable form mixed with a pharmaceutically acceptable carrier. The carrier may be solid or liquid, depending on the type and/or location of administration selected.

Techniques and compositions for making useful dosage forms using the present invention are described in one or more of the following references: Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, New York, 1990; Katzung, ed., Basic and Clinical Pharmacology, Ninth Edition, McGraw Hill, 2007; Goodman and Gilman, eds., The Pharmacological Basis of Therapeutics, Tenth Edition, McGraw Hill, 2001; Remington's Pharmaceutical Sciences, 20th Ed., Lippincott Williams & Wilkins., 2000; Martindale, The Extra Pharmacopoeia, Thirty-Second Edition (The Pharmaceutical Press, London, 1999); all of which are incorporated by reference, and the like, relevant portions incorporated herein by reference.

For example, diNACA, NACA-$d_3$, di-NACA-$d_6$, or combinations thereof, may be included in a tablet. Tablets may contain, e.g., suitable binders, lubricants, disintegrating agents, coloring agents, flavoring agents, flow-inducing agents and/or melting agents. For example, oral administration may be in a dosage unit form of a tablet, gelcap, caplet or capsule, the active drug component being combined with an non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol, mixtures thereof, and the like. Suitable binders for use with the present invention include: starch, gelatin, natural sugars (e.g., glucose or beta-lactose), corn sweeteners, natural and synthetic gums (e.g., acacia, tragacanth or sodium alginate), carboxymethylcellulose, polyethylene glycol, waxes, and the like. Lubricants for use with the invention may include: sodium oleate, sodium stearate, magnesium stearate, sodium benzoate, sodium acetate, sodium chloride, mixtures thereof, and the like. Disintegrators may include: starch, methyl cellulose, agar, bentonite, xanthan gum, mixtures thereof, and the like.

DiNACA, NACA-$d_3$, di-NACA-do, or combinations thereof, may be administered in the form of liposome delivery systems, e.g., small unilamellar vesicles, large unilamallar vesicles, and multilamellar vesicles, whether charged or uncharged. Liposomes may include one or more: phospholipids (e.g., cholesterol), stearylamine and/or phosphatidylcholines, mixtures thereof, and the like.

DiNACA, NACA-$d_3$, di-NACA-do, or combinations thereof, may also be coupled to one or more soluble, biodegradable, bioacceptable polymers as drug carriers or as a prodrug. Such polymers may include: polyvinylpyrrolidone, pyran copolymer, polyhydroxylpropylmethacrylamide-phenol, polyhydroxyethylasparta-midephenol, or polyethyleneoxide-polylysine substituted with palmitoyl residues, mixtures thereof, and the like. Furthermore, diNACA may be coupled one or more biodegradable polymers to achieve controlled release of the diNACA, biodegradable polymers for use with the present invention include: polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels, mixtures thereof, and the like.

As used herein, the term "pharmaceutically acceptable salts" refers to derivatives of the disclosed compounds, wherein the parent compound is modified by making acid or base salts thereof. Examples of pharmaceutically acceptable salts include, but are not limited to, mineral or organic acid salts of the basic residues. The pharmaceutically acceptable salts include the conventional quaternary ammonium salts of the parent compound formed, for example, from non-toxic inorganic or organic acids. These salts can be prepared in situ in the administration vehicle or the dosage form manufacturing process, or by separately reacting a purified compound of the invention in its free base form with a suitable organic or inorganic acid, and isolating the salt thus formed during subsequent purification. For example, such conventional non-toxic salts include, but are not limited to, those derived from inorganic and organic acids selected from 1,2-ethanedisulfonic, 2-acetoxybenzoic, 2-hydroxyethanesulfonic, acetic, ascorbic, benzenesulfonic, benzoic, bicarbonic, bisulfonic, carbonic, citric, edetic, ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauric, lauryl sulfonic, maleic, malic, mandelic, methanesulfonic, napsylic, naphthylic, nitric, oleic, oxalic, palimitic, pamoic, pantothenic, phenylacetic, phosphoric, polygalacturonic, propionic, salicyclic, stearic, succinic, sulfamic, sulfanilic, sulfuric, tannic, tartaric, toluenesulfonic, and valeric.

A dosage unit for use of the diNACA, NACA-$d_3$, di-NACA-$d_6$, or combinations thereof, of the present invention, may be a single compound or mixtures thereof with other compounds, e.g., a potentiator. The compounds may be mixed together, form ionic or even covalent bonds. The deuterated-N-acetyl cysteine amide of the present invention may be administered in oral, intravenous (bolus or infusion), intraperitoneal, subcutaneous, or intramuscular form, all using dosage forms well known to those of ordinary skill in the pharmaceutical arts. Depending on the particular location or method of delivery, different dosage forms, e.g., tablets, capsules, pills, powders, granules, elixirs, tinctures, suspensions, syrups, gels, solutions, and emulsions may be used to provide the deuterated-N-acetyl cysteine amide of the present invention to a patient in need of therapy that includes $D_3$-N-acetyl cysteine amide.

Deuterated-N-acetyl cysteine amide is typically administered in admixture with suitable pharmaceutical salts, buffers, diluents, extenders, excipients and/or carriers (collectively referred to herein as a pharmaceutically acceptable carrier or carrier materials) selected based on the intended form of administration and as consistent with conventional pharmaceutical practices. Depending on the best location for administration, the deuterated-N-acetyl cysteine amide may be formulated to provide, e.g., maximum and/or consistent dosing for the particular form for oral, rectal, topical (including ophthalmic), inhalation, intranasal, injection (intravenous or intraocular) or parenteral administration. While the deuterated-N-acetyl cysteine amide may be administered alone, it will generally be provided in a stable form or derivatives thereof mixed with a pharmaceutically acceptable carrier. The carrier may be solid or liquid, depending on the type and/or location of administration selected.

The skilled artisan will recognize that deuterium (2H) is a stable, non-radioactive isotope of 1H hydrogen and has an atomic weight of 2.014. Hydrogen naturally occurs as a mixture of the isotopes: hydrogen (1H), deuterium (2H), and tritium (3H). The skilled artisan recognizes that in all chemical compounds with an H atom, the H atom actually represents a mixture of 1H, 2H, and 3H, where about 0.015% is deuterium. Thus, compounds with a level of deuterium that has been enriched to be greater than its natural abundance of 0.015% are considered unnatural and, as a result, novel over their non-enriched counterparts.

The deuterium-enriched NACA-$d_3$, di-NACA-do, or combinations thereof described herein includes deuterium enrichment for NACA-$d_3$, di-NACA-$d_6$, or combinations thereof and optionally in other locations in the compound. Deuterium-enrichment reduces the rate at which the two enantiomers of NACA-$d_3$, di-NACA-do, or combinations thereof may interconvert. Further, the deuterium-enriched NACA-$d_3$, di-NACA-do, or combinations thereof described herein is provided in enantiomerically pure form. This enantiomerically pure, NACA-d3, di-NACA-$d_6$, or combinations thereof provides for a better therapeutic agent than non-deuterated diNACA and/or racemic mixtures of the compound.

The present invention provides deuterium-enriched compounds for use in the therapeutic methods and pharmaceutical compositions described herein. The deuterium-enriched compounds are provided in high enantiomeric purity in order to maximize therapeutic benefit, such as maximal potency per dose of therapeutic agent and minimize adverse side effects, such as off-target effects.

In one embodiment, gelatin capsules (gelcaps) may include deuterated-N-acetyl cysteine amide, diNACA, or both and powdered carriers, such as lactose, starch, cellulose derivatives, magnesium stearate, stearic acid, and the like. Like diluents may be used to make compressed tablets. Both tablets and capsules may be manufactured as immediate-release, mixed-release or sustained-release formulations to provide for a range of release of medication over a period of minutes to hours. Compressed tablets may be sugar coated or film coated to mask any unpleasant taste and protect the tablet from the atmosphere. An enteric coating may be used to provide selective disintegration in, e.g., the gastrointestinal tract.

The NACA-d3, di-NACA-$d_6$, or combinations thereof may be administered in the form of liposome delivery systems, e.g., small unilamellar vesicles, large unilamallar vesicles, and multilamellar vesicles, whether charged or uncharged. Liposomes may include one or more: phospholipids (e.g., cholesterol), stearylamine and/or phosphatidylcholines, mixtures thereof, and the like.

The NACA-d3, di-NACA-do, or combinations thereof may also be coupled to one or more soluble, biodegradable, bioacceptable polymers as drug carriers or as a prodrug. Such polymers may include: polyvinylpyrrolidone, pyran copolymer, polyhydroxylpropylmethacrylamide-phenol, polyhydroxyethylasparta-midephenol, or polyethyleneoxide-polylysine substituted with palmitoyl residues, mixtures thereof, and the like. Furthermore, the deuterated-N-acetyl cysteine amide may be coupled one or more biodegradable polymers to achieve controlled release of the deuterated-N-acetyl cysteine amide, biodegradable polymers for use with the present invention include: polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacylates, and crosslinked or amphipathic block copolymers of hydrogels, mixtures thereof, and the like.

The present invention is directed to the use of an implant with NACA-$d_3$, di-NACA-do, or combinations thereof to treat age-related macular degeneration, glaucoma, and/or diabetic retinopathy. In one embodiment, the present invention includes a method for the treatment of age-related macular degeneration in a human that comprises administering to the human therapeutically effective amount of NACA-d3, di-NACA-$d_6$, or combinations thereof. In some embodiments, the NACA-d3, di-NACA-$d_6$, or combinations thereof is provided in or with a pharmaceutically acceptable carrier. In other embodiments, the NACA-d3, di-NACA-$d_6$, or combinations thereof implant is administered in or about the eye, e.g., intraocularly, subretinally, intravitreally, posterior juxtascleral, anterior juxtascleral, retrobulbar, intramuscularly, or topically. The implants of the present invention can be injected into one or more non-limiting locations, such as pre-determined locations, that can include, e.g., intravitreal, intrastromal, intracameral, subtenon, retinal, subretinal, retrobulbar, peribulbar, suprachoroidal, subchoroidal, conjunctival, subconjunctival, episcleral, posterior juxtascleral, anterior juxtascleral, circumcorneal, topical, and tear duct.

Administration of a therapeutic agent such as an antioxidant through the use of one or more intraocular implants may improve the treatment of ocular diseases or conditions involving oxidative stress. Implants comprise a pharmaceutically acceptable polymeric composition and are formulated to release one or more pharmaceutically active agents over an extended period of time. In certain embodiments involving the delivery of one agent, the dosage regimen may be formulated to provide one drug to the anterior or posterior segment of the eye. For example, for ocular drug delivery to the posterior region of the eye, the implant would likely be introduced as an intravitreal implant, inserted into the vitreous cavity.

In certain embodiments involving the delivery of more than one agent, the dosage regiment may be formulated to provide two or more drugs to the posterior segment of the eye under different dosage regimens. For example, the dosage of the antioxidant in an implant may be made to be discontinuous over the treatment period while a non-discontinuous dosage of an auxiliary agent is administered in an implant over the same overall time period. The implant containing the antioxidant and the implant containing the auxiliary agent may be different implants or the same implant comprising means of differentially administering the antioxidant and auxiliary agent, such means including different coatings or shells which may contain, neither, one or both drugs, or covalent linkage of one or both drugs to a biodegradable polymer of the implant by way of a biodegradable linkage, thus permitting regulation of the delivery of one or more drug over the time of the treatment. The implants are effective to provide a therapeutically effective dosage of the agent or agents directly to a region of the eye to treat one or more ocular diseases or conditions involving oxidative stress. Thus, with a single administration, therapeutic agents will be made available at the site where they are needed and may be maintained for an extended period of time, rather than subjecting the patient to repeated injections or, in the case of self-administered drops, ineffective treatment with only limited bursts of exposure to the active agent or agents.

One such intraocular implant in accordance with the disclosure herein comprises a therapeutic component and a drug release sustaining component associated with the therapeutic component. In accordance with the present invention, the therapeutic component comprises, consists essentially of, or consists of: NACA-d3, di-NACA-do, or combinations thereof. The drug release sustaining component is associated with the therapeutic component to sustain release of a therapeutically effective amount of the antioxidant into an eye in which the implant is placed. The therapeutic amount of the antioxidant is released into the eye for a period of time greater than about two months after the implant is placed in the eye.

For the purposes of this description, we use the following terms as defined in this section, unless the context of the word indicates a different meaning.

As used herein, an "intraocular implant" refers to a device or element or drug product that is structured, sized, or otherwise configured to be placed "in an eye", including the subconjunctival space. Intraocular implants are generally biocompatible with physiological conditions of an eye and do not cause adverse side effects. Intraocular implants may be placed in an eye without disrupting vision of the eye.

As used herein, a "therapeutic component" refers to a portion of an intraocular implant comprising one or more therapeutic agents or substances used to treat a medical condition of the eye. The therapeutic component may be a discrete region of an intraocular implant, or it may be homogenously distributed throughout the implant. The therapeutic agents of the therapeutic component are typically ophthalmically acceptable, and are provided in a form that does not cause adverse reactions when the implant is placed in an eye.

As used herein, a "drug release sustaining component" refers to a portion of the intraocular implant that is effective to provide a sustained release of the therapeutic agents of the implant. A drug release sustaining component may be a biodegradable polymer matrix, or it may be a coating covering a core region of the implant that comprises a therapeutic component.

As used herein, "associated with" means mixed with, dispersed within, coupled to, covering, or surrounding. With respect to intraocular implants which comprise a therapeutic component associated with a biodegradable polymer matrix, "associated with" specifically excludes biodegradable polymeric coatings that may be provided on or around the matrix.

As used herein, an "ocular region" or "ocular site" refers generally to any area of the eyeball, including the anterior and posterior segment of the eye, and which generally includes, but is not limited to, any functional (e.g., for vision) or structural tissues found in the eyeball, or tissues or cellular layers that partly or completely line the interior or exterior of the eyeball. Specific examples of areas of the eye in an ocular region include the anterior chamber, the posterior chamber, the vitreous cavity, the choroid, the suprachoroidal space, the conjunctiva, the subconjunctival space, the episcleral space, the intracorneal space, the epicorneal space, the sclera, the pars plana, surgically-induced avascular regions, the macula, and the retina.

As used herein, an "ophthalmic or ocular disease" or "ophthalmic or ocular condition" is a disease, ailment or condition which affects or involves the eye or one of the parts or regions of the eye. Broadly speaking the eye includes the eyeball, or globe, the tissues and fluids which constitute the eye, the periocular muscles (such as the oblique and rectus muscles) and the portion of the optic nerve which is within or adjacent to the eye.

An anterior ocular condition is a disease, ailment or condition which affects or which involves an anterior (i.e. front of the eye) ocular region or site, such as a periocular muscle, an eye lid or an eye ball tissue or fluid which is located anterior to the posterior wall of the lens capsule or ciliary muscles. Thus, an anterior ocular condition primarily affects or involves the conjunctiva, the cornea, the anterior chamber, the iris, the posterior chamber (behind the retina but in front of the posterior wall of the lens capsule), the lens or the lens capsule and blood vessels and nerve which vascularize or innervate an anterior ocular region or site.

An anterior ocular condition can include a disease, ailment, or condition, such as for example, aphakia; pseudophakia; astigmatism; blepharospasm; cataract; conjunctival diseases; conjunctivitis; corneal diseases; corneal ulcer; dry eye syndromes; eyelid diseases; lacrimal apparatus diseases; lacrimal duct obstruction; myopia; presbyopia; pupil disorders; refractive disorders and strabismus. Glaucoma can also be considered to be an anterior ocular condition because a clinical goal of glaucoma treatment can be to reduce a hypertension of aqueous fluid in the anterior chamber of the eye (i.e., reduce intraocular pressure).

A posterior ocular condition is a disease, ailment or condition which primarily affects or involves a posterior ocular region or site such as choroid or sclera (in a position posterior to a plane through the posterior wall of the lens capsule), vitreous, vitreous chamber, retina, optic nerve (i.e., the optic disc), and blood vessels and nerves which vascularize or innervate a posterior ocular region or site.

As used herein, the term "biodegradable" refers to a material that will breakdown to soluble species or that will degrade under physiologic conditions to smaller units or chemical species that are, themselves, non-toxic (biocompatible) to the subject and capable of being metabolized, eliminated, or excreted by the subject. The terms biodegradable, bioabsorbable, and bioerodible as used herein are equivalent and are used interchangeably herein.

As used herein, the term "nonbiodegradable" refers to a material that will not breakdown to soluble species or that will not degrade under physiologic conditions to smaller units or chemical species that are, themselves, non-toxic (biocompatible) to the subject and capable of being metabolized, eliminated, or excreted by the subject. The terms nonbiodegradable, nonbioerodible and nonbioabsorbable as used herein are equivalent and are used interchangeably herein.

As used herein, the term "biodegradable polymer" refers to a polymer or polymers which degrade in vivo, and wherein erosion or breakdown of the polymer or polymers over time occurs concurrently with or subsequent to release of the therapeutic agent. Specifically, hydrogels such as methylcellulose which act to release drug through polymer swelling are specifically excluded from the term "biodegradable polymer". A biodegradable polymer may 'be a homopolymer, a copolymer, or a polymer comprising more than two different polymeric units.

Oral Solutions or Suspensions. For oral administration in a liquid dosage form, the oral drug components may be combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, surfactants, coloring agents, and melting agents, mixtures thereof, and the like.

Liquid dosage forms for oral administration may also include coloring and flavoring agents that increase patient acceptance and therefore compliance with a dosing regimen.

Parenteral Solutions. Solutions for parenteral administration include generally, a water-soluble salt of the active ingredient, suitable stabilizing agents, and if necessary, buffering salts. In general, water, a suitable oil, saline, aqueous dextrose (e.g., glucose, lactose and related sugar solutions) and glycols (e.g., propylene glycol or polyethylene glycols) may be used as suitable carriers for parenteral solutions. Antioxidizing agents such as sodium bisulfite, sodium sulfite and/or ascorbic acid, either alone or in combination, are suitable stabilizing agents. Citric acid and its salts and sodium EDTA may also be included to increase stability. In addition, parenteral solutions may include pharmaceutically acceptable preservatives, e.g., benzalkonium chloride, methyl- or propyl-paraben, and/or chlorobutanol. Suitable pharmaceutical carriers are described in Remington's Pharmaceutical Sciences, Mack Publishing Company, a standard reference text in this field, relevant portions incorporated herein by reference.

Topical Lotions, Gels, Creams, Solutions or Suspensions. For topical administration in a liquid dosage form, the drug components may be combined with numerous non-toxic, pharmaceutically acceptable inert excipients such as ethanol, glycerol, water, and some non-aqueous moieties. Formulations may be sterile or non-sterile. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, thickeners, viscosity-modifiers, surfactants, coloring agents, and melting agents, mixtures thereof, and the like.

Capsules. Capsules may be prepared by filling standard two-piece hard gelatin or hydroxypropyl methylcellulose capsules each with 10 to 500 milligrams of powdered active ingredient, 5 to 150 milligrams of lactose, 5 to 50 milligrams of cellulose and 6 milligrams magnesium stearate.

Soft Gelatin Capsules. A mixture of active ingredient is dissolved in a digestible oil such as soybean oil, cottonseed oil or olive oil. The active ingredient is prepared and injected by using a positive displacement pump into gelatin to form soft gelatin capsules containing, e.g., 100-500 milligrams of the active ingredient. The capsules are washed and dried.

Tablets. A large number of tablets are prepared by conventional procedures so that the dosage unit was 100-500 milligrams of active ingredient, 0.2 milligrams of colloidal silicon dioxide, 5 milligrams of magnesium stearate, 50-275 milligrams of microcrystalline cellulose, 11 milligrams of starch and 98.8 milligrams of lactose. Appropriate coatings may be applied to increase palatability or delay absorption.

To provide an effervescent tablet appropriate amounts of, e.g., monosodium citrate and sodium bicarbonate, are blended together and then roller compacted, in the absence of water, to form flakes that are then crushed to give granulates. The granulates are then combined with the active ingredient, drug and/or salt thereof, conventional beading or filling agents and, optionally, sweeteners, flavors and lubricants.

Injectable solution. A parenteral composition suitable for administration by injection is prepared by stirring 1.5% by weight of active ingredient in deionized water and mixed with, e.g., up to 10% by volume propylene glycol and water. The solution is made isotonic with sodium chloride and sterilized using, e.g., ultrafiltration.

Suspension. An aqueous suspension is prepared for oral administration so that each 5 ml contain 100 mg of finely divided active ingredient, 200 mg of sodium carboxymethyl cellulose, 5 mg of sodium benzoate, 1.0 g of sorbitol solution, U.S.P., and 0.025 ml of vanillin.

Inhalation or Intranasal formulation. An inhalation or intranasal formulation includes a solution, suspension, semi-solid formulation, dry powder, or other formulation administered intranasally.

Injectable Formulation. A sterile injectable formulation includes a solution or suspension that is suitable for intramuscular, intravenous, intraocular (including intravitreal or intracameral) or subcutaneous administration. Such injectable formulations are isosmotic, usually with osmaolarity similar to isotonic 0.9% saline solution, and PH balanced, usually with a neutral pH.

For mini-tablets, the active ingredient is compressed into a hardness in the range 6 to 12 Kp. The hardness of the final tablets is influenced by the linear roller compaction strength used in preparing the granulates, which are influenced by the particle size of, e.g., the monosodium hydrogen carbonate and sodium hydrogen carbonate. For smaller particle sizes, a linear roller compaction strength of about 15 to 20 KN/cm may be used.

As used herein, the term "chewable" refers to semi-soft, palatable and stable chewable treat without addition of water. It should be appreciated to the skilled artisan that a chewable composition will be stable and palatable, fast disintegrating, semi-soft medicated chewable tablets (treats) by extrusion without the addition of extraneous water. A soft chewable tablets does not harden on storage and are resistant to microbial contamination. A semi-soft chewable contain a blend of any one or more of binders, flavors, palatability enhancers, humectants, disintegrating agents, non-aqueous solvents, and diluents that are plasticized with liquid plasticizers, such as glycols and polyols to make them ductile and extrudable. The chewable can be made by extrusion, e.g., including fats or lipids as plasticizers and binding agents, is manufactured in the absence of added water, uses plasticizers to replace water in extrudable matrices, contains humectants to maintain the extrudable chew in a pliant and soft state during its shelf life, or any combination thereof. The chewable form may be provided in conjunction with one or more flavorings and/or taste masking agents that improve the taste of the . . . formulation greater than 10, 20, 30, 40, 50, 60, 70, 80, or 90%. The chewable can include the active agent and the ion exchange resin to enhance taste masking.

Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorings and coloring agents. Parenteral and intravenous forms may also include minerals and other materials to make them compatible with the type of injection or delivery system chosen.

Enantiopurity. The present invention covers both the R and S enantiomers of diNACA. The natural enantiomer, i.e., the enantiomer found in nature for cysteine is L-cysteine. When L-cysteine is converted by chemical synthesis to diNACA with no racemization, the result is di-L-NACA which is equivalent to (2R,2R')-3,3'-disulfanediyl bis(2-acetamidopropanamide). The opposite enantiomer is obtained when D-cysteine is converted by chemical synthesis to NACA with no racemization to yield di-D-NACA which is equivalent to (2S,2S')-3,3'-disulfanediyl bis(2-acetamidopropanamide).

Enantiopurity. The present invention covers both the R and S enantiomers of NACA-$d_3$. The natural enantiomer, i.e., the enantiomer found in nature for cysteine is L-cysteine. When L-cysteine is converted by chemical synthesis to NACA with no racemization, the result is N-acetyl-L-cysteine amide, which is equivalent to (R)-2-acetylamino-3-mercapto-propamide. The opposite enantiomer is obtained when D-cysteine is converted by chemical synthesis to NACA with no racemization to yield N-acetyl-L-cysteine amide, which is equivalent to(S)-2-acetylamino-3-mercapto-propamide.

Metabolism. An advantage of diNACA over N-acetylcysteine amide (NACA) is the reduction in metabolism rate compared to NACA. DiNACA has a longer plasma half-life than NACA. The major metabolites of diNACA are NACA and N-acetylcysteine (NAC) afforded by cleavage of the sulfur bond of diNACA to yield NACA and NAC. Dosing the patient with diNACA affords high greater bioavailability in tissues like the retina and aqueous humor compared to dosing with NACA, presumably due the higher lipophilicity of diNACA compared to NACA and the resulting in vivo cleavage to two NACA-like molecules, thereby effectively increasing the half-life of NACA in the body.

Metabolism. Deuterium-inhibition of NACA metabolism. An advantage of NACA-d3, di-NACA-$d_6$, or combinations thereof, is the reduction in metabolism rate compared to the non-deuterated NACA. Non-deuterated NACA has a plasma half-life of approximately 2 hours in fasting subjects and approximately 6 hours in fed subjects. The major metabolite of NACA is N-acetylcysteine (NAC) afforded by deamidation of the primary amide functional group of NACA by tissue (e.g., plasma or other tissue) amidase. Another metabolite of NACA is cysteine afforded by (a) deamidation of the primary amide functional group of NACA by tissue (e.g., plasma or other tissue) amidase and (b) de-acetylation of the secondary amide functional group of NACA by tissue (e.g., plasma or other tissue) amidase. Replacement of the acetyl methyl group hydrogen atoms with deuterium atoms slows down the action of tissue amidases on both (primary and secondary) amide functional groups of NACA-d3, di-NACA-$d_6$, or combinations thereof, thereby prolonging its residence time in the body, i.e., increasing the half-life in the body.

Example 1

Preparation of (2R,2R')-3,3'-disulfanediyl bis(2-acetamidopropanamide) (diNACA). A process for preparing (2R, 2R')-3,3'-disulfanediyl bis(2-acetamidopropanamide) is described. The inventors used various approaches to make diNACA and found the most advantageous route as shown in Steps 1-3. To generate the diNACA, Step 1 (01NPI01-01) was performed in a 2000 L glass-lined reactor using 67 kg of L-cystine. The material was treated with methanol (1323 kg, 25 vol) and thionyl chloride (80 kg, 2.41eq) and agitated for 1 hour before heating to reflux. Once the In-Process Control (IPC) sample met the criteria of less than 1% of L-cystine remaining, the reaction was deemed complete. After cooling to 20±5° C. the methanol was exchanged with methyl t-butylether and the product isolated by filtration. Due to the scale, the isolation occurred in three portions with the first and some of the second portion being carried forward without drying. The remainder of the material was dried under vacuum to yield L-cystine dimethylester dihydrochloride.

Step 1 Formation of L-Cystine Dimethylester Dihydrochloride.

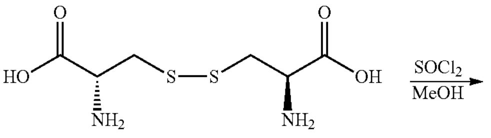

L-Cystine
$C_6H_{12}N_2O_4S_2$
Mol Wt: 240.29

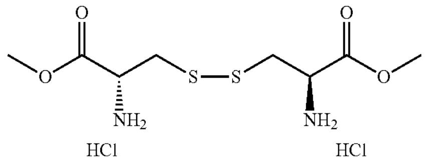

L-Cystine Dimethylester Dihydrochloride
$C_8H_{16}N_2O_4S_2$
Mol Wt: 341.26

TABLE 1

| Reference | 01NPI01-01 |
|---|---|
| | To clean 2000 L reactor charged |
| 67 kg | of L-Cystine and |
| 1323 kg | of polish filtered Methanol, began agitation. Cooled the reactor contents to −10 ± 5 °C, via diaphragm pump, slowly charged |
| 80 kg | of Thinyl Chloride maintaining the internal temperature at ≤−5 °C. Heated reactor contents to 20 ± 5 °C and allowed to agitate for 1 hour. Furthermore, heated reactor contents to reflux (~65 to 70 °C) and allowed to agitate for 16 hours. Reaction deemed complete by HPLC analysis. |
| | Withdrew representative sample; submitted to QC laboratory for HPLC analysis. |

Step 1.30 - IPC for Reaction Completion (L-Cystine ▶ L-Cystine Dimethylester Dihydrochloride)

| 01NPI01 | L-Cystine | L-Cystine Dimethylester | Reaction |
|---|---|---|---|
| −01-30 | 2.7% | 97% | Complete |

| | |
|---|---|
| | Cooled reactor contents to 20 ± 5 °C. Meanwhile, set up the reactor with a scrubber. To the scrubber charged |
| 114 kg | of 4M Sodium Hydroxide, aqueous solution. Set reactor jacket temperature to 15 °C. Vacuum distilled reactor contents until 402 L remained. Through polish filter charged |

TABLE 1-continued

| Reference | | 01NPI01-01 |
|---|---|---|
| 3 x 297 | kg | of Methyl tert-Butyl Ether, continued to vacuum distill until 402 L remained in the reactor while not exceeding jacket temperature of 45° C. Set jacket temperature to 15 °C, through polish filter, charged |
| 297 | kg | of Methyl tert-Butyl Ether and allowed the contents to agitate with an internal temperature of 20 ± 5 °C for 1 hour. The reactor contents were filtered portionwise through Nutsche Filter and rinsed with |
| 148.5 | kg | of polish filtered Methyl tert-Butyl Ether. Wet L-Cystine Dimethylester Dihydrochloride was transferred into drying trays and dried to constant weight at ≤ 45° C. to afford 3 portions totaling 40.6 kg of L-Cystine Dimethylester Dihydrochloride. L-Cystine Dimethylester Dihydrochloride ready for use in the next step |

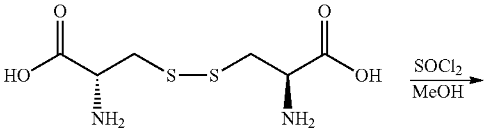

L-Cystine
$C_6H_{12}N_2O_4S_2$
Mol Wt: 240.29

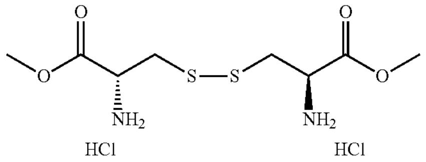

L-Cystine Dimethylester
Dihydrochloride
$C_8H_{16}N_2O_4S_2$
Mol Wt: 341.26

TABLE 2

| Reagents/Materials | MW | Eqs. | Moles | Density | Expected Amt (kg) |
|---|---|---|---|---|---|
| L-Cystine, ≥98.5% | 240.29 | 1.0 | 279 | — | 67 |
| Thinonyl Chloride, ≥97% | 118.97 | 2.41 | 672 | 1.64 | 80 |
| Methanol (MeOH), ≥99% | 32.04 | 25 vol | — | 0.79 | 1323 |
| 50% (w/w) Sodium Hydroxide, aqueous solution (for scrubber) | 40.00 | — | — | 1.515 | 25 |
| Process Water, Filtered (for scrubber) | 18.02 | — | — | 1.00 | 95 |
| Methyl-tert Butyl Ether (MTBE), ≥99% | 88.15 | 26 vol | — | 0.74 | 1287 |

Step 2 was carried out in a 2000 L glass-lined reactor by treating 44 kg of L-cystine dimethylester dihydrochloride with acetonitrile (799 kg, 23 vol), cooling to 0±5° C. and sparging with nitrogen for 30 minutes. Triethylamine (55 kg, 4.2 eq) was added followed by slow addition of acetic anhydride (28 kg, 2.1eq) while maintaining the internal temperature at ≤5° C. The reaction was stirred for 30 minutes and then sampled until the IPC met the criteria for completion, less than 1% of L-cystine dimethylester dihydrochloride remaining. Upon reaction completion, the reaction was diluted with ethyl acetate (396 kg, 10 vol) and washed with sat. aqueous $NaHCO_3$ (2×92 kg). The aqueous layer was back extracted with ethyl acetate (198 kg, 5 vol) and the combined organic layers were dried with sodium sulfate. The drying agent was filtered away and the solution subjected to sequential solvent exchanges consisting of acetonitrile (2×139 kg) followed by ethyl acetate (4×238 kg) resulting in a slurry of DiNACMe in EtOAc. The material was filtered, washed with ethyl acetate and dried under vacuum to yield 45.05 kg (100%) of DiNACMe. A second run was performed as described to give 42.05 kg (100%) of DiNACMe.

Step 2 Formation of Di-NACMe

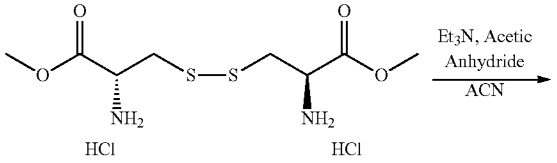

L-Cystine Dimethylester
Dihydrochloride
$C_8H_{16}N_2O_4S_2$
Mol Wt: 341.26

-continued

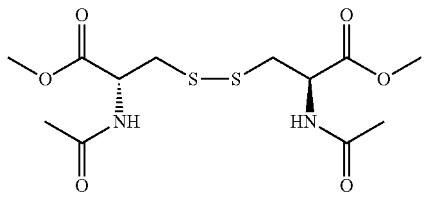

Di-NACMe
$C_{12}H_{20}N_2O_6S_2$
Mol Wt: 352.42

TABLE 3

| Reagents/Materials | MW | Eqs. | Moles | Density | Expected Amt (kg) |
|---|---|---|---|---|---|
| L-Cystine Dimethylester Dihydrchloride, ≥95% | 341.26 | 1.0 | 129 | — | 44 |
| Acetonitrile, ≥99% | 41.05 | 23 vol | — | 0.79 | 799 |
| Triethylamine (TEA), ≥99% | 101.19 | 4.2 | 544 | 0.73 | 55 |
| Acetic Anhydride, ≥99% | 102.09 | 2.1 | 274 | 1.08 | 28 |
| Sodium Bicarbonate, ≥99% (for 9% (w/w) $NaHCO_3$ (aq) soln) | 58.44 | 0.378 mass eq. | — | — | 18 |
| Process Water, Filtered (for Aqueous solution above) | 18.02 | — | — | 1.00 | 176 |
| Sodium Sulfate, anhydrous | 142.04 | — | — | — | * |
| Ethyl Acetate, ≥99% | 88.1 | 41 vol | — | 0.90 | 1625 |

TABLE 4

| Reference | 01NPI02-01 |
|---|---|
| | To clean 2000 L reactor charged |
| | of L-Cystine Dimethylester Dihydrochloride (charged wet solids total |
| 44 kg | weight charged 52.3 kg), and |
| | of polish filtered Acetonitrile. Bubbled nitrogen into the contents of the |
| 799 kg | reactor for 30 minutes and cooled the reactor to 0 ± 5 °C. While maintaining the |
| | internal temperature ≤5 °C slowly, charged |
| | of Triethylamine, |
| 55 kg | of Acetic Anhydride and allowed contents to agitate with an internal |
| 28 kg | temperature of 0 ± 5 °C for 30 minutes. Reaction deemed complete by HPLC |
| | analysis. |
| | Withdrew representative sample; submitted to QC laboratory for HPLC analysis. |

Step 2.32 - IPC for Reaction Completion (L-Cystine Dimethylester Dihydrochloride ▶ Di-NACMe)

| 01NPI02 | L-Cystine Dimethylester Dihydrochloride | Di-NACMe | Reaction |
|---|---|---|---|
| −01-32 | 0.7% | 99.3% | Incomplete |
| −01-32-1 | 0.5% | 99.5% | Complete |
| −02-32 | 0.1% | 99.9% | Complete |

| | |
|---|---|
| | Charged |
| 396 kg | of filtered Ethyl Acetate and with agitation warmed the reactor contents to |
| | 20 ± 5 °C. To the reactor charged |
| 2 × 92 kg | of 9% (w/w) Sodium Bicarbonate, aqueous solution, allowed phase |
| | separation each time. Dropped aqueous phase into clean HDPE drum labeled |
| | Step 2.39 - Aqueous Layer and Organic Layer into a clean drum labeled; |
| | Step 2.44 - Di-NACMe in ACN/EtOAc. |
| 198 kg | To the reactor charged the contents of the drum labeled Step 2.39 - Aqueous. |
| | Layer and |
| | of filtered Ethyl Acetate allowed contents to agitate for 25 minutes. Allowed |
| | layers to separate, drained bottom layer into drum labeled; Step 2.48 - |
| 5.0 kg | Aqueous Layer and organic layer into clean drum labeled Step 2.44 - Di- |
| | NACMe in ACN/EtOAc. To each drum (total 8) labeled Step 2.44 - Di- |
| | NACMe in ACN/EtOAc charged |
| | of Sodium Sulfate, anhydrous, agitated each drum with drum agitator for 5 |
| | minutes. To clean reactor charged, as room allowed, the contents of drums |
| 2 × 139 kg | labeled Step 2.44 - Di-NACMe in ACN/EtOAc through a bag filter followed |
| | by a polish filter. Vacuum distilled the contents until all drums have been |
| | charged and rinsed. Continued distillation until 220 L remained in the reactor. |
| | Through a polish filter, charged |
| | of Acetonitrile and vacuum distilled until 220 L remained in the reactor. |
| | Withdrew representative sample; submitted to QC laboratory for GC analysis. |

Step 2.72 - IPC for Residual Triethylamine by GC

| 01NPI02 | IPC Limit (ppm) | Actual Value (ppm) |
|---|---|---|
| −01-72 | Report >7020 | 158,244 |

| | |
|---|---|
| 4 × 238 kg | Charged, through polish filter |
| | of Ethyl Acetate, vacuum distilled until 220 L remained in the reactor. |
| | Agitated contents of the reactor with internal temperature of 0 ± 5 °C for |

TABLE 4-continued

| Reference | 01NPI02-01 |
|---|---|
| 79 kg | 1 hour, filtered through Nutsche filter in two portions. Rinsed each portion with of polish filtered Ethyl Acetate. Blown dry contents of the filter for at least 20 minutes with 10 ± 5 psig of nitrogen. Transferred wet (EtOAc) Di-NACMe filter cake into pre lined vacuum trays and dried to constant weight at ≤25 °C to afford 45.05 kg of dry Di-NACMe. Di-NACMe ready for processing in the next step. This procedure was repeated as 01NPI02-02. |

Step 3 was performed by first sparging 28-30% ammonium hydroxide (244 kg, 8.44 eq) with nitrogen for 30 minutes. The solution was then cooled to 0±5° C. and 87.1 kg of DiNACMe added. The solution was stirred at 0±5° C. for 4 hours before sampling. The IPC showed 0.1% DiNACMe remaining and was deemed complete. The ammonium hydroxide was distilled to ~87 L and exchanged with degassed ethanol (3×344 kg) to a volume of ~87 L. Upon completion of the solvent exchanges, degassed ethanol (344 kg, 4 vol) was added and the slurry stirred for 1 hour at 0±5° C. The material was filtered, washed with degassed ethanol and dried under vacuum to yield 50.25 kg (63%) of diNACA.

Step 3A, the recrystallization of diNACA from water, was performed in a 200 L glass-lined reactor. Batch 01NPI03A-01 involved the recrystallization of 25.1 kg of diNACA from degassed water (151 kg, 6 vol) to yield 17.05 kg of diNACA. The remaining 25.1 kg of diNACA was recrystallized in batch 01NPI03A-02 to give 17.5 kg of diNACA. Both lots of recrystallized diNACA were combined (34.55 kg) and recrystallized a final time in batch 01NPI03A-03 to give 28.3 kg of purified diNACA.

Step 3 Generation of diNACA.

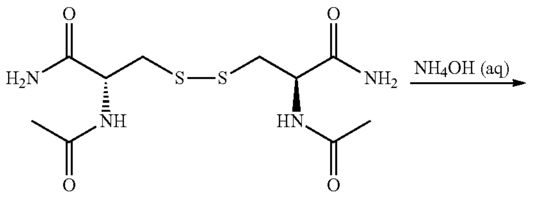

Di-NACMe
$C_{10}H_{18}N_4O_4S_2$
Mol Wt: 322.40

-continued

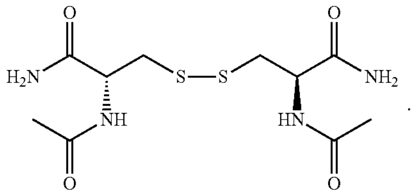

Di-NACA
$C_{10}H_{18}N_4O_4S_2$
Mol Wt: 322.40

TABLE 5

| Reagents/Materials | MW | Egs. | Moles | Density | Expected Amt (kg) |
|---|---|---|---|---|---|
| DiNACA | 352.42 | 1.0 | 247 | — | 87.1 |
| 28-30% Ammonium Hydroxide | 35.05 | 8.44 | 2088 | 0.9 | 244 |
| Ethanol, absolute 200 proof | 46.07 | 17 vol | — | 0.79 | 1170 |

TABLE 6

| Reference | 01NPI03-01 |
|---|---|
| 244 kg | To 2000 L Reactor charged, via diaphragm pump, of 28-30% Ammonium Hydroxide, with agitation bubbled 3 ± 2 psig of nitrogen into the contents through the diptube for 30 minutes. Pressurized the reactor with 3 ± 2 psig of nitrogen and cooled the contents to 0 ± 5 °C. Through |
| 87.1 kg | solid shoot apparatus charged of Di-NACMe and allowed contents to agitate with internal temperature of 0 ± 5 °C for 4 hours. Reaction deemed complete by HPLC analysis. Withdrew representative sample; submitted to QC laboratory for HPLC analysis. |

| Step 3.28 - IPC for Reaction Completion (Di-NACMe ► DiNACA) | | | |
|---|---|---|---|
| 01NPI03 | Di-NACMe | DINACA | Reaction |
| -01-28 | 0.1 % | 99.9% | Complete |

Set the reactor jacket temperature for 15 °C and vacuum distilled the contents until ~87 L remained in the reactor not exceeding jacket temperature of 45 °C.

TABLE 6-continued

| Reference | 01NPI03-01 |
|---|---|
| 3 × 344 kg | Charged through a polish filter of degassed Ethanol, Absolute, 200 Proof and distilled the contents each time until ~87 L remained in the reactor. |
| 344 kg | Charged through a polish filter of degassed Ethanol, Absolute, 200 Proof, cooled reactor contents to 0 ± 5 °C and agitated for 1 hour with in internal temperature of 0 ± 5 °C. Verified the reactor contained a thick, filterable slurry of solids. Reactor |
| 69 kg | contents were filtered in two portions through Nutsche filter, rinsed each portion with of degassed Ethanol, Absolute, 200 Proof and blown filter contents dry for at least 20 minutes with 10 ± 5 psig of nitrogen. Transferred wet- DiNACA filter cake into pre lined vacuum trays and dried to constant weight at ≤45 °C to afford total of 50.52 kg of DiNACA. DiNACA ready for processing in the next step. |

Step 3A Purification of DiNACA

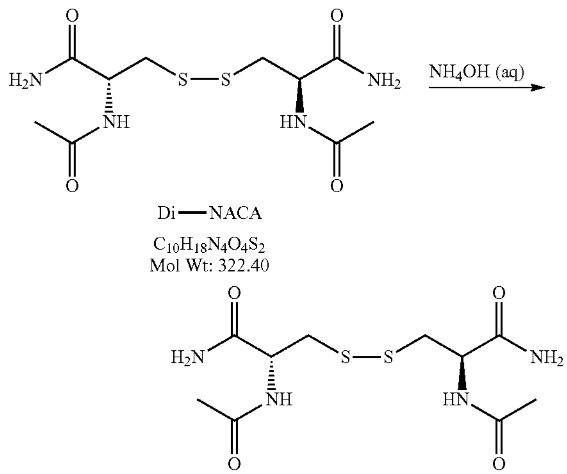

Di—NACA
$C_{10}H_{18}N_4O_4S_2$
Mol Wt: 322.40

Di—NACA
$C_{10}H_{18}N_4O_4S_2$
Mol Wt: 322.40

.

TABLE 7

| Reagents/Materials | MW | Eqs. | Moles | Density | Expected Amt (kg) |
|---|---|---|---|---|---|
| DiNACA | 322.40 | 1.0 | 77.9 | — | 25.1 |
| Process Water, Filtered | 18.02 | 8 vol | — | 1.0 | 201 |

TABLE 8

| Reference | 01NPI03A-01 |
|---|---|
| | To 2000 L Reactor charged |
| 151 kg | of Process Water, Filtered. Reactor contents were agitated degassed for at least 30 minutes. While maintaining nitrogen blanket charged to the reactor |
| 25.1 kg | of DiNACA, heated contents to reflux (~100 °C) and agitated at reflux until complete solution was obtained. Once complete solution obtained, cooled the reactor contents to 20 ± 5 °C. Reactor contents were agitated at 20 + 5 °C for at 3 hours, filtered via Nutsche Filter, rinsed with |
| 50.0 kg | of degassed Process Water, Filtered. Transferred wet-DiNACA filter cake into pre lined vacuum trays and dried to constant weight at ≤45 °C to afford total of 17.05 kg of DiNACA. |

TABLE 8-continued

| Reference | 01NPI03A-01 |
|---|---|
| | DiNACA ready for processing in the next step. This procedure was repeated as 01NPI03A-02 and 01NPI03A-03. |

FIG. 1 is an X-Ray Powder Diffractogram for (2R,2R')-3,3'-disulfanediyl bis(2-acetamidopropanamide) of the present invention.

Figure 2:
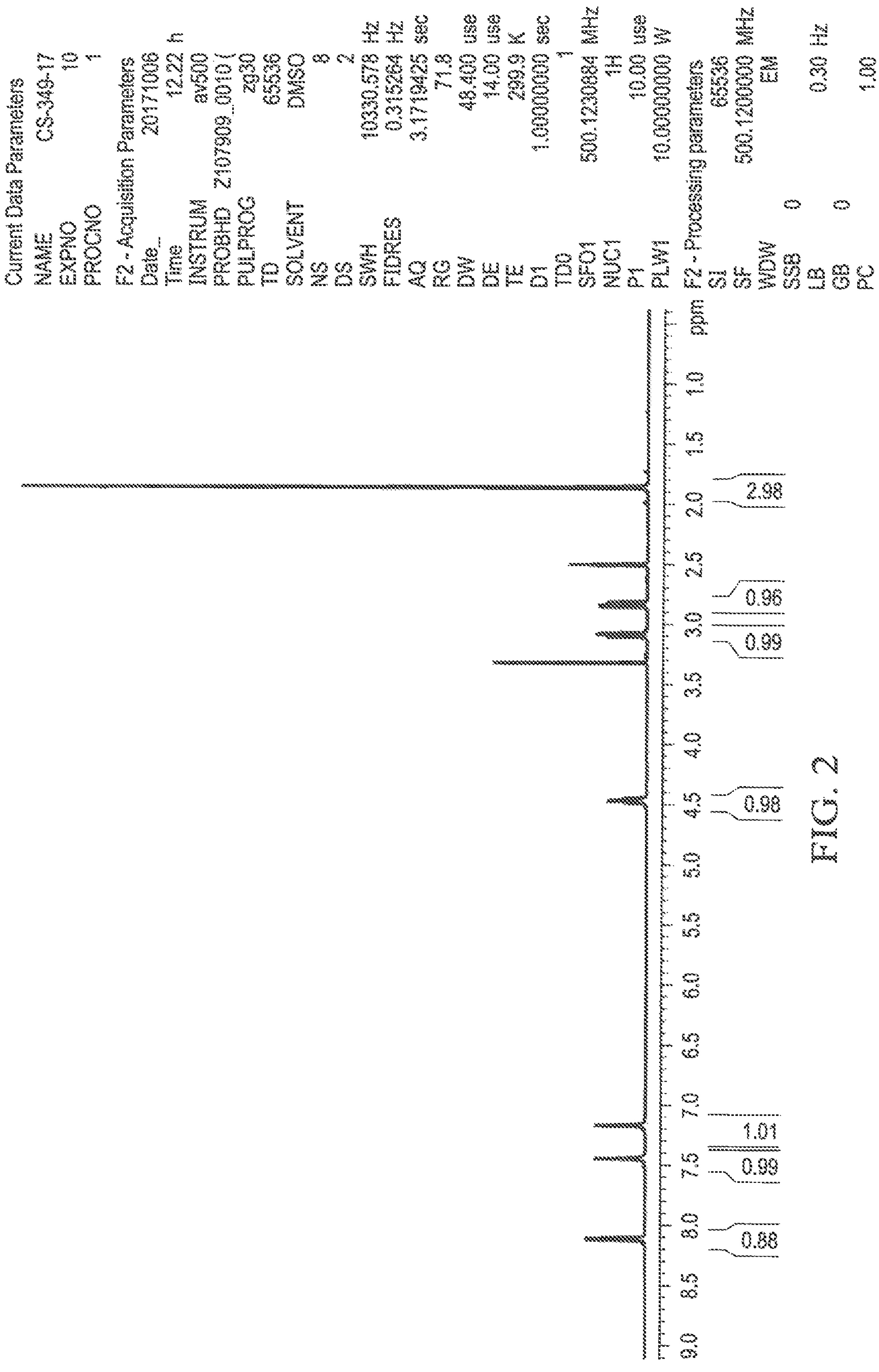
FIG. 2 shows proton nuclear magnetic spectrum for (2R,2R')-3,3'-disulfanediyl bis(2-acetamidopropanamide) of the present invention.

FIG. 2 shows proton nuclear magnetic spectrum for (2R,2R')-3,3'-disulfanediyl bis(2-acetamidopropanamide) of the present invention.

FIG. 3 shows heteronuclear single quantum correlation spectrum for (2R,2R')-3,3'-disulfanediyl bis(2-acetamidopropanamide) of the present invention.

FIG. 4 shows heteronuclear multiple-bond correlation spectrum for (2R,2R')-3,3'-disulfanediyl bis(2-acetamidopropanamide) of the present invention.

Figure 5:
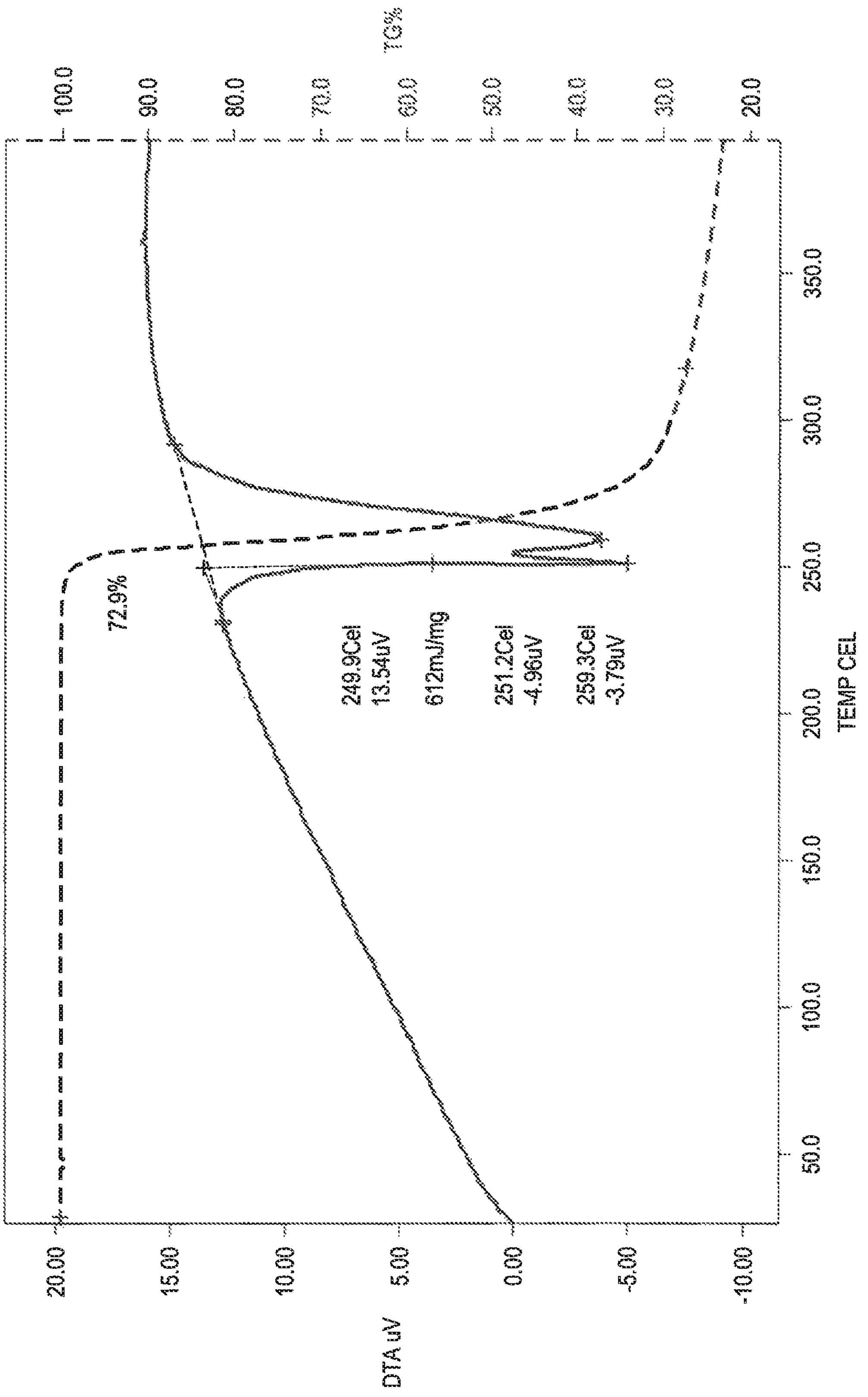
FIG. 5 shows a combination thermogravimetric and differential thermal analysis for (2R,2R')-3,3'-disulfanediyl bis (2-acetamidopropanamide) of the present invention.

FIG. 5 shows a combination thermogravimetric and differential thermal analysis for (2R,2R')-3,3'-disulfanediyl bis (2-acetamidopropanamide) of the present invention.

Figure 6:
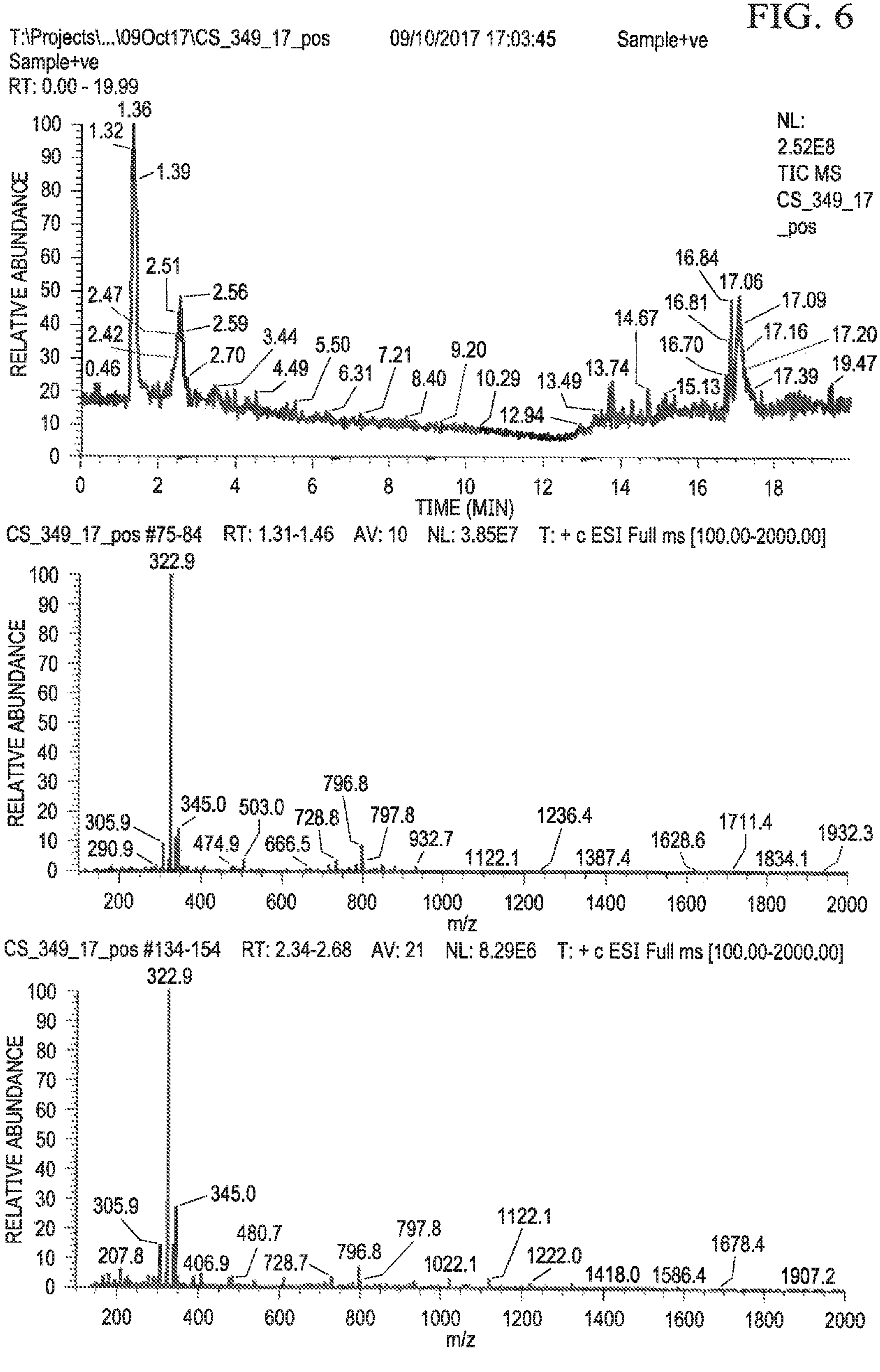
FIG. 6 shows liquid chromatographic mass spectrometric data for (2R,2R')-3,3'-disulfanediyl bis(2-acetamidopropanamide) of the present invention.

FIG. 6 shows liquid chromatographic mass spectrometric data for (2R,2R')-3,3'-disulfanediyl bis(2-acetamidopropanamide) of the present invention.

Example 2. Ophthalmic Suspension

Sodium phosphate, propylene glycol, Pluronic F127, edetate disodium benzalkonium chloride are dissolved in 800 ml of water. The pH is adjusted with dilute HCl or NaOH. DiNACA is added. The osmolarity is within 250 to 350 mOsm Kg. Solution is q.s. with water to a total of 1 liter. The formulation is sterilized by autoclave. This is only one ophthalmic formulation and does not exclude other solution formulations.

TABLE 9

| Component | Quantity |
|---|---|
| diNACA | 1g to 100 g |
| Sodium phosphate | 0.8 g |
| Propylene glycol | 18 g |
| Pluronic F127 | 50 g |
| Edetate disodium | 0.1 g |
| Benzalkonium chloride | 0.1 g |
| 0.1N HCl or NaOH | Adjust pH to 7.4 |
| Water for Injection | Q.S. 1000 ml |

Compounds described herein can be provided in isolated or purified form. Isolated or purified compounds are a group of compounds that have been separated from their environment, such as from a crude reaction mixture if made in a laboratory setting or removed from their natural environment if naturally occurring. Examples of the purity of the isolated compound include, for example, at least 50%, 55%, 60%, 65%, 70%, 75%, 80%, 85%, 90%, 95%, to 100% by weight.

Another aspect of the invention provides a unit quantum of a compound described herein, such as an amount of at least (a) one microgram of a disclosed compound, (b) one mg, or (c) one gram. In further embodiments, the quantum is, for example, at least 0.01, 0.02, 0.03, 0.04, 0.05, 0.1, 0.2, 0.3, 0.4, 0.5, or 1 mole of the compound. The present amounts also cover lab-scale (e.g., gram scale including 1, 2, 3, 4, 5 g, etc.), kilo-lab scale (e.g., kilogram scale including 1, 2, 3, 4, 5 kg, etc.), and industrial or commercial scale (e.g., multi-kilogram or above scale including 100, 200, 300, 400, 500 kg, etc.) quantities as these will be more useful in the actual manufacture of a pharmaceutical. Industrial/commercial scale refers to the amount of product that would be produced in a batch that was designed for clinical testing, formulation, sale/distribution to the public, etc.

Doses of a compound provided herein, or a pharmaceutically acceptable salt thereof, vary depending on factors such as: specific indication to be treated; age and condition of a patient; and amount of a second active agent used, if any. Generally, a compound provided herein, or a pharmaceutically acceptable salt thereof, may be used in an amount of from about 0.1 mg to about 1 g per day, or from about 0.1 mg to about 500 mg per day, and can be adjusted in a conventional fashion (e.g., the same amount administered each day of the treatment), in cycles (e.g., one week on, one week off), or in an amount that increases or decreases over the course of treatment. In other embodiments, the dose can be from about 1 mg to 1000 mg, from about 1 mg to about 450 mg, from about 0.1 mg to about 150 mg, from about 1 mg to about 300 mg, from about 10 mg to about 100 mg, from about 0.1 mg to about 50 mg, from about 1 mg to about 50 mg, from about 10 mg to about 50 mg, from about 20 mg to about 30 mg, or from about 1 mg to about 20 mg. In yet other embodiments, the daily dose can be from about 50 mg to 75 mg, 75 mg to 100 mg, 100 mg to 125 mg, 125 mg to 150 mg, 150 mg to 175 mg, 175 mg to 200 mg, 200 mg to 225 mg, 225 mg to 250 mg, 250 mg to 275 mg, 275 mg to 300 mg, 300 mg to 325 mg, 325 mg to 350 mg, 350 mg to 375 mg, 375 mg to 400 mg, 400 mg to 425 mg, or 425 mg to 450 mg. In certain embodiments, (2R,2R')-3,3'-disulfanediyl bis(2-acetamidopropanamide) is administered at a daily dosage in the range of about 125 mg to 150 mg, 150 mg to 175 mg, 175 mg to 200 mg, 200 mg to 225 mg, 225 mg to 250 mg, 250 mg to 275 mg, or 275 mg to 300 mg. In certain embodiments, (2R,2R')-3,3'-disulfanediyl bis(2-acetamidopropanamide) is administered at a daily dosage in the range of about 50 mg to 75 mg, 75 mg to 100 mg, 100 mg to 125 mg, 125 mg to 150 mg, 150 mg to 175 mg, 175 mg to 200 mg, 200 mg to 225 mg, 225 mg to 250 mg, 250 mg to 275 mg, or 275 mg to 300 mg. In certain embodiments, (2R,2R')-3,3'-disulfanediyl bis(2-acetamidopropanamide) is administered at a daily dosage in the range of about 125 mg to 150 mg or 150 mg to 175 mg. In certain embodiments, (2R,2R')-3,3'-disulfanediyl bis(2-acetamidopropanamide) is administered at a daily dosage in the range of about 125 mg to 175 mg. In certain embodiments, (2R,2R')-3,3'-disulfanediyl bis(2-acetamidopropanamide) is administered at a daily dosage in the range of about 140 mg to 160 mg. In yet other embodiments, (2R,2R')-3,3'-disulfanediyl bis(2-acetamidopropanamide) is administered at a daily dosage in the range of about 50 mg to 175 mg, or about 125 mg to 175 mg. In yet other embodiments, the daily dose is less than about 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, or 450 mg. In yet other embodiments, the daily dose is less than about 125 mg, 150 mg, or 175 mg. The formulation may also exclude non-active ingredients, in which case the formulation will "consist essentially" of the active agents claimed herein, as non-active ingredients. The formulation may also exclude all other ingredients, in which case the formulation will "consist" of the active agents. Each of these variants are contemplated herein.

Example 3. Preparation of NACA-$d_3$

A process for preparing 10 mg of $D_3$-N-acetyl cysteine amide 5 (NACA-$d_3$) is described. The inventors used various approaches to make $D_3$-N-acetyl cysteine amide by using the chemistry shown in Scheme 1. In each case, the inventors observed a mixture of compounds while forming the methyl ester 3 and LCMS suggests that several other compounds were made, including 4 in addition to the desired 3. Treatment of this mixture with ammonium hydroxide gave 6, with no observation of the desired 5 by LCMS.

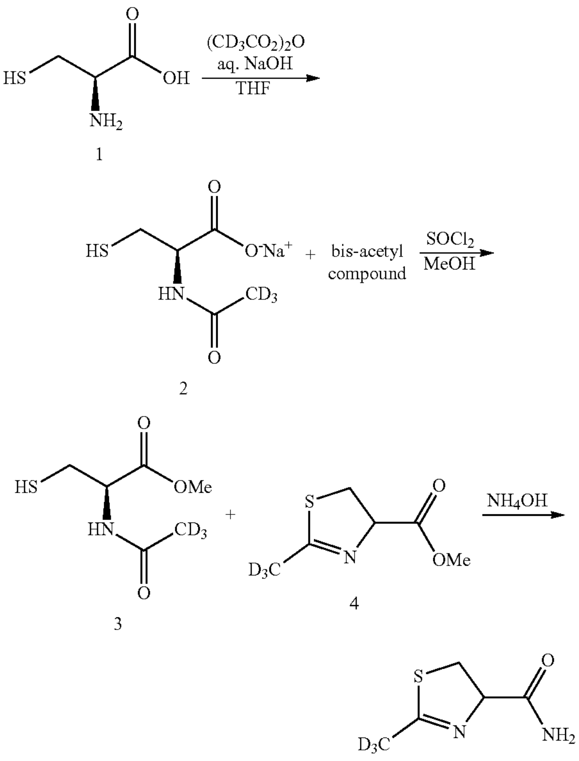

1
2
3
4
6

Cysteine methyl ester 7 (Scheme 2) allows the elimination of the problematic transformation of 2 to 3. Acetylation affords 3 directly from 7 and then reaction with ammonium hydroxide provides the target compound 5.

Scheme 2.

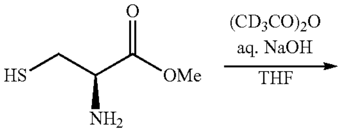

7

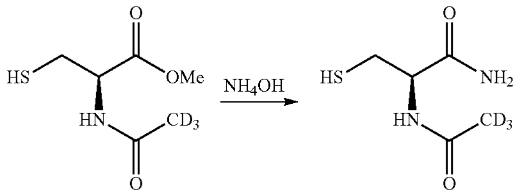

3

5

TABLE 10

| Reaction | Notebook | Scale (g) | Yield (%) | Comments |
|---|---|---|---|---|
| 1 to 2 | 1719-TTP-2 | 0.50 | N/A | 2 eq. of NaOH, 1 eq. anhydride. LCMS shows a mixture of 2 and bis-acetyl. |
| 2 to 3 | 1719-TTP-3 | 0.78 | N/A | LCMS shows a mixture of 3 and 4. |
| 3 to 5 | 1719-TTP-4 | 0.38 | N/A | LCMS shows a mass for 6. |
| 1 to 2 | 1719-TTP-5 | 0.50 | N/A | 3 eq. NaOH, 2 eq. anhydride. Clean bis-acetyl by crude $^1$H NMR. |
| 2 to 3 | 1719-TTP-6 | 0.96 | N/A | LCMS shows a mixture of 3 and 4. |
| 3 to 5 | 1719-TTP-7 | 0.23 | N/A | LCMS shows a mass for 6. |
| 1 to 2 | 1719-TTP-8 | 0.50 | N/A | With 3.0 equiv NaOH and 2.0 equiv. anhydride. Clean bis-acetyl by crude $^1$H NMR. |
| 2 to 3 | 1719-TTP-9 | 0.96 | N/A | Carefully monitored by LC-MS. Formation of 4 is competitive with 3. |
| 3 to 5 | 1719-TTP-10 | 0.93 | N/A | LCMS shows mass for 6. |
| 1 to 2 | 1719-TTP-11 | 0.50 | N/A | Precisely 2.0 eq. of NaOH, 1.0 eq. anhydride. LCMS shows a mixture of 2 and bis-acetyl. Underway. |

TABLE 11

| N-2-acetyl-L-cysteineamide-$d_3$ | | |
|---|---|---|
| Test | Acceptance Criteria | Result |
| Appearance | Report Only | White crystalline solid |
| Purity | 95% or better | >95% by NMR |
| $^1$H NMR Spectrum ($DMSO-d_6$) | Consistent with structure | Consistent with structure[1] |
| Mass Spectrum | Consistent with structure | Consistent with structure[2] |
| Isotopic Abundance | 97% or better $D_3$ with no detectable $D_0$ | No $D_2$, $D_1$, or $D_0$ detected by NMR.[3] |

1. $^1$H NMR Spectrum also shows 1.52% w/w water, and 0.28% w/w ethanol. No visible acetate protons.
2. MS (ESI+) for $C_5H_7D_3N_2O_2S$ m/z 188.0 (M+Na)+: MS (ESI−) for $C_5H_7D_3N_2O_2S$ m/z 164.0 (M−H).
3. Mass peaks are visible at 185.0 (ESI$^+$) and 162.0 (ESI') but we do not believe these are due to Do or Di species, respectively.

Figure 7:
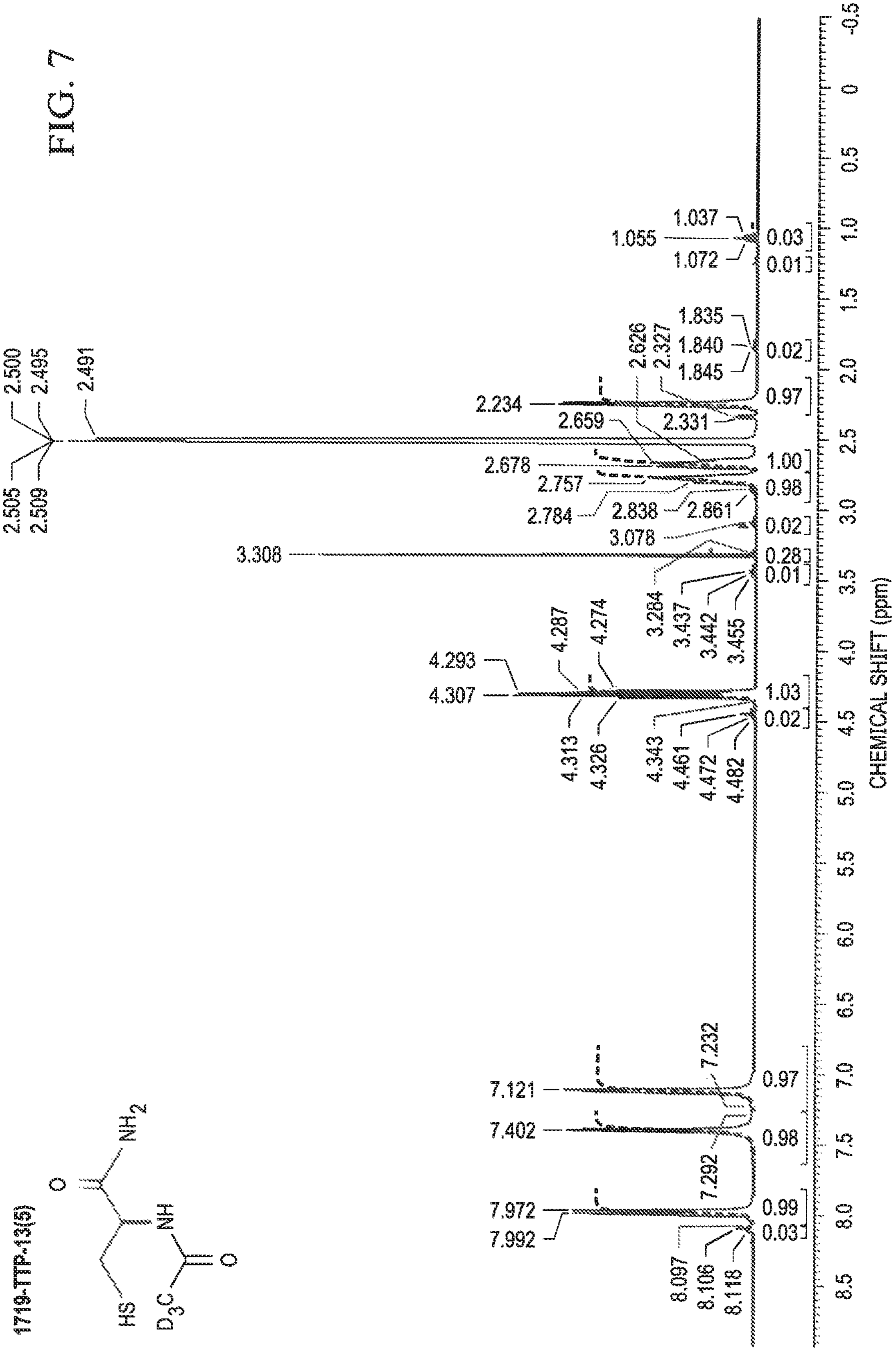
FIG. 7 shows chemical shift data for one batch of the N-2-acetyl-L-cysteineamide-$d_3$ (NACA-$d_3$) of the present invention.

FIG. 7 shows chemical shift data for one batch of the N-2-acetyl-L-cysteineamide-$d_3$ of the present invention.

Figure 8:
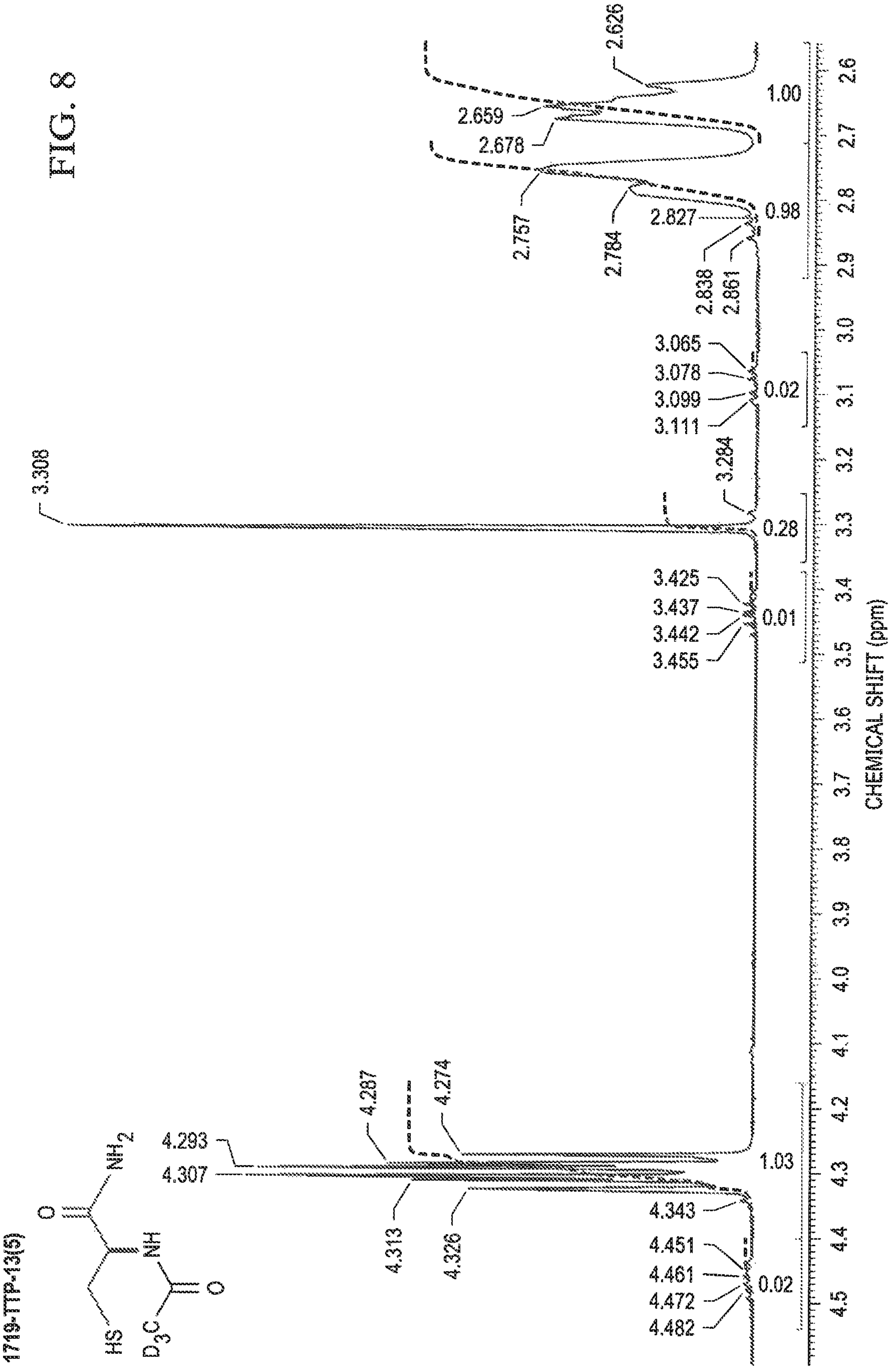
FIG. 8 shows additional chemical shift data for another batch of the N-2-acetyl-L-cysteineamide-$d_3$ of the present invention.

FIG. 8 shows chemical shift data for another batch of the N-2-acetyl-L-cysteineamide-$d_3$ of the present invention.

Figure 9:
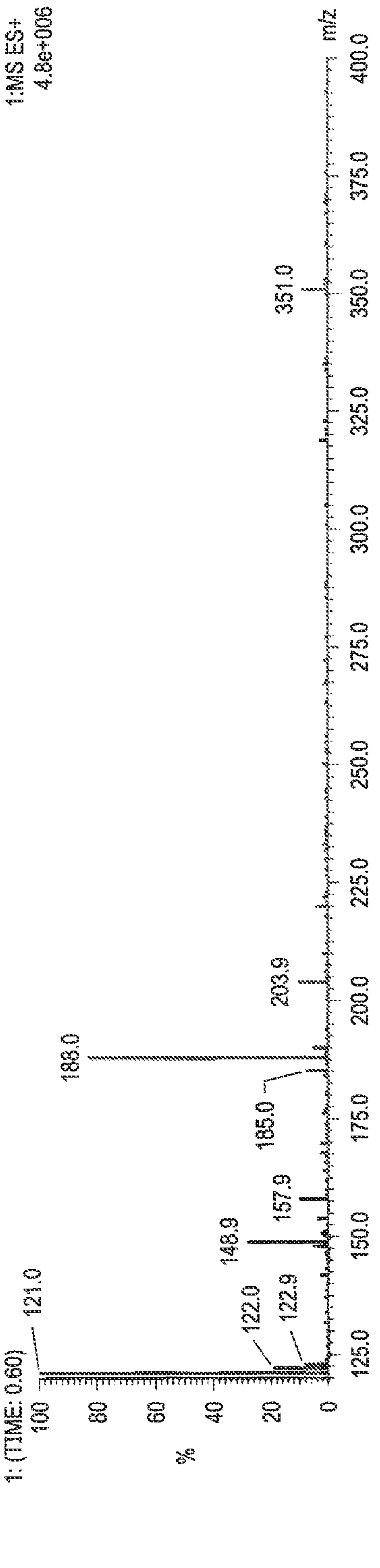
FIG. 9 shows MS results the N-2-acetyl-L-cysteineamide-$d_3$ of the present invention.

FIG. 9 shows MS results the N-2-acetyl-L-cysteineamide-$d_3$ of the present invention.

Figure 10:
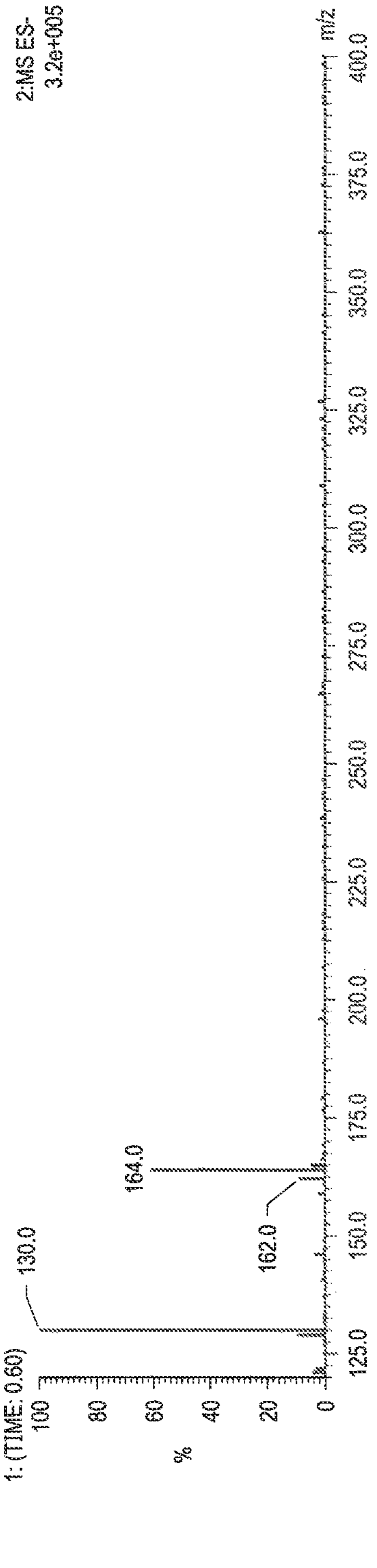
FIG. 10 shows additional MS results of the N-2-acetyl-L-cysteineamide-$d_3$ of the present invention.

FIG. 10 shows MS results the N-2-acetyl-L-cysteine-amide-$d_3$ of the present invention.

Example. Oral Formulation. NACA-$d_3$ is dissolved in a mixture of water and Ora-Sweet®. Ora-Sweet is a commercially available syrup vehicle containing water, sucrose, glycerin, sorbitol, flavoring, buffering agents (citric acid and/or sodium phosphate), methyl paraben and potassium sorbate, pH 4.2 manufactured by Paddock Laboratories, Inc., Minneapolis, Minnesota. ORA-SWEET has a cherry syrup flavor. Neat NACA-$d_3$ has a mild sulfur odor. When mixed with ORA-SWEET there is no odor and the taste is that of ORA-SWEET only. ORA-SWEET is a pale pink clear solution. The lowest concentration of NACA-$d_3$ (250 mg/100 ml ORA-SWEET) is a pale pink clear solution while the highest concentration of NACA-$d_3$ (4,000 mg/100 ml ORA-SWEET) is a very pale pink clear solution Instructions for Preparation of NACA-$d_3$ Oral Solution:

1. Weigh NACA-$d_3$[either 250, 750, 1500, 3000 or 4000 mg (+1 mg), as appropriate for the particular dose group] and place into a 125 mL (approximately) capacity opaque high density polyethylene, labeled bottle with opaque polypropylene screw cap.
2. Measure 50 mL of Purified Water and pour into each bottle containing NACA-$d_3$ and shake vigorously by hand (at least 30 seconds) to dissolve.
3. Measure 50 mL Ora-Sweet and pour into each bottle containing NACA-$d_3$.
   a. Shake vigorously by hand (at least 30 seconds) to dissolve.
   b. This solution may be stored for up to 8 hours at room temperature (20° C.±5° C.), protected from light. (If solution is not consumed after these storage conditions, do not use, i.e., dispose and document.
4. Immediately prior to dosing, shake well for 10 seconds.
5. Provide to subject.
6. Have subject drink total contents of bottle.
7. Pour another 20 ml of Ora-Sweet into bottle, cap and shake vigorously for 5 seconds (this is "rinse #1).
8. Have subject drink total contents of bottle.
9. Pour another 20 ml of Ora-Sweet into bottle, cap and shake vigorously for 5 seconds (this is "rinse #2).

Have subject drink total contents of bottle (resulting in an approximately total volume of 140 ml Ora-Sweet mixture consumed by each subject for each dose regimen).

Example 4. NACA-$d_3$ Ophthalmic Solution

Sodium phosphate, propylene glycol, Pluronic F127, edetate disodium benzalkonium chloride are dissolved in 800 ml of water. The pH is adjusted with dilute HCl or NaOH. NACA-$d_3$ is added. The osmolarity is within 250 to 350 mOsm Kg. Solution is q.s. with water to a total of 1 liter. The formulation is sterilized by autoclave. This is only one ophthalmic formulation and does not exclude other solution formulations.

TABLE 12

| Component | Quantity |
|---|---|
| NACA-$d_3$ | 1g to 100 g |
| Sodium phosphate | 0.8 g |
| Propylene glycol | 18 g |

TABLE 12-continued

| Component | Quantity |
|---|---|
| Pluronic F127 | 50 g |
| Edetate disodium | 0.1 g |
| Benzalkonium chloride | 0.1 g |
| 0.1N HCl or NaOH | Adjust pH to 7.4 |
| Water for Injection | Q.S. 1000 ml |

Example 5. Preparation of Di-NACA-$d_6$

N,N'-Diacetyl-L-Cystine-1,1'-dimethyl ester-$d_6$:

Triethylamine (4.3 mL, 31 mmol) was added to commercial L-Cystine dimethyl ester dihydrochloride (2.5 g, 7.3 mmol) in dry acetonitrile (40 mL) at 0° C. under an argon atmosphere. Acetic anhydride-$d_6$ (1.7 g, 16 mmol) was added and the mixture was stirred for 1.5 h under argon. The reaction was quenched with 1 M deuterium chloride in $D_2O$, extracted with ethyl acetate, washed sequentially with saturated $NaHCO_3$ and brine, dried ($MgSO_4$), filtered and concentrated in vacuo to give a white solid which was used directly in the next step (1.58 g, 60%).

$^1$H NMR (500 MHz, $CDCl_3$) δ 6.54 (s, 1H, NH), 6.52 (s, 1H, NH), 4.84 (m, 2H, 2×CH), 3.75 (s, 6H, 2×$CH_3$), 3.18 (m, 4H, 2×$CH_2$).

(2R,2R')-3,3'-Disulfanediyl bis(2-acetamidopropanamide), Di-NACA-$d_6$:

Ammonium hydroxide (28%, 83 mL) was added to methyl ester (1.58 g, 4.4 mmol) at 0° C. under an argon atmosphere. A white precipitate slowly formed. After 3 h the solvent was removed in vacuo by azeotroping with ethanol (×3). The crude material was recrystallised twice with water and dried under high vacuum giving a white crystalline solid 650 mg (45%).

$^1$H NMR (500 MHz, DMSO-$d_6$) δ 8.14-8.19 (m, 2H, 2×NH), 7.42-7.58 (m, 2H, $NH_2$), 7.15-7.23 (m, 2H, $NH_2$), 4.41-4.56 (m, 2H, 2×NCH), 3.02-3.29 (m, 2H, $SCH_2$), 2.81-2.89 (m, 2H, $SCH_2$).

$^{13}$C NMR (500 MHz, DMSO-$d_6$) δ 172.45 (2×C=O), 169.95 (2×C=O), 52.15 (2×NCH), 41.43 (2×$SCH_2$), 22.36 (2×$CD_3$).

High-resolution Mass Spectrum of diNACA-$d_6$: Found m/z 351.1047. $C_{10}H_{12}D_6N_4O_4S_2Na$ [M+Na]+ requires m/z 351.1044. The deviation of 0.9 ppm is within normally accepted limits for the establishment of identity by HRMS. No signal for do material was seen (detection limit about 0.5%).

HPLC Chromatogram of diNACA-de reveals a main peak at 3.323 minutes with 98.2 area %.

HPLC Analysis Conditions:

Column: Phenomenex Luna C18 (2) 5 μm 250×4.6 mm

Guard Column: Phenomenex Security Guard C18 RP 4×3 mm

Mobile Phase A: 0.1% TFA in water

Mobile Phase B: ACN

Gradient (A: B): T0=90:10, T24=40:60, T25=90:10

Flow Rate: 1.0 mL/min

Sample solvent: Mobile phase

Sample Concentration: ~1 mg/mL

Column Temperature: 25° C.

Injection Volume: 10 μL

Detection: UV 253 nm

Synthetic Scheme: Preparation of Di-NACA-$d_6$'

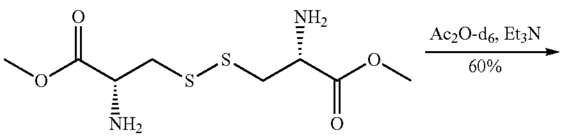

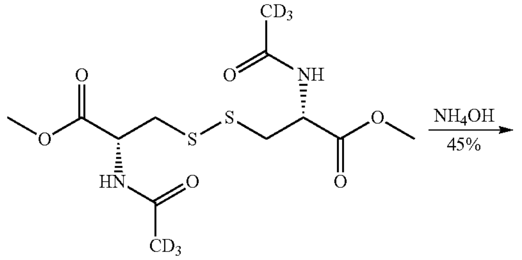

N,N'-Diacetyl-, L-Cystine 1,1'-dimethyl ester-d6

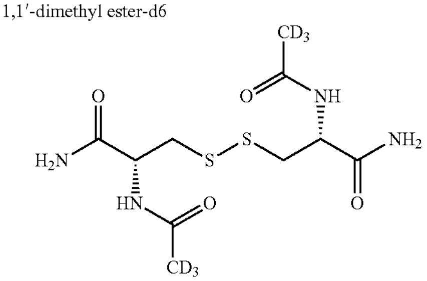

Di-NACA-d6

TABLE 13

| | |
|---|---|
| Name | Di-NACA-$d_6$ |
| CAS Number: | 16359-16-3 (unlabelled) |
| Structure: | 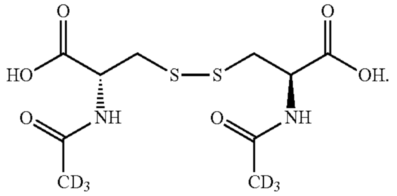 [SMILES: [2H]C([2H])([2H])C(=O)N[C@@H](CSSC[C@H](NC(=O)C([2H])([2H])[2H])C(=O)O)C(=O)O] |
| Molecular Weight: | $C_{10}H_{12}D_6N_4O_4S_2$ = 328.44 |
| Appearance: | White, crystalline solid |
| Purity By HPLC: | 98.8% |

Figure 11:
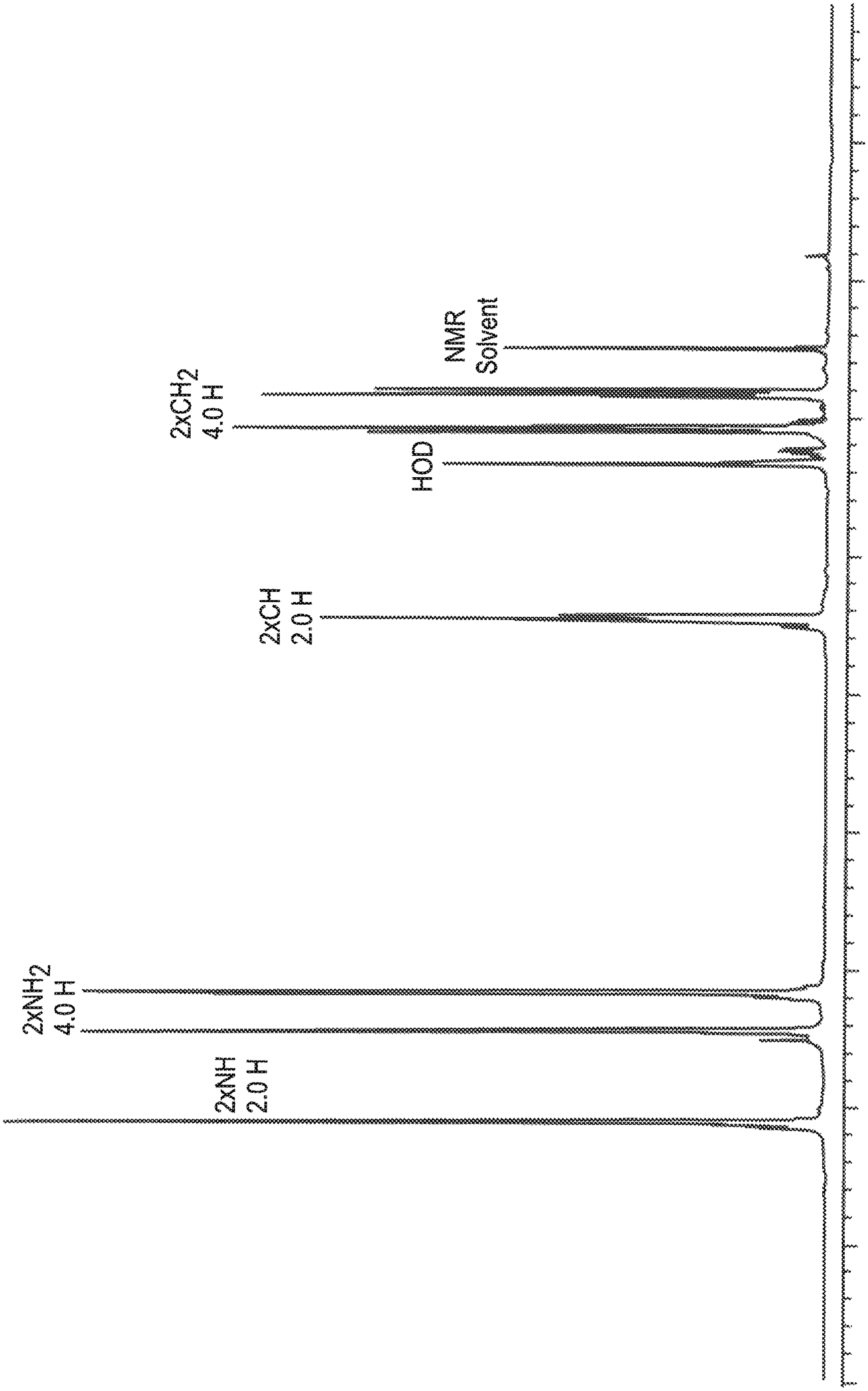
FIG. 11 is a Proton NMR Spectrum of diNACA-$d_6$.

FIG. 11 is a Proton NMR Spectrum of diNACA-$d_6$.

Figure 12:
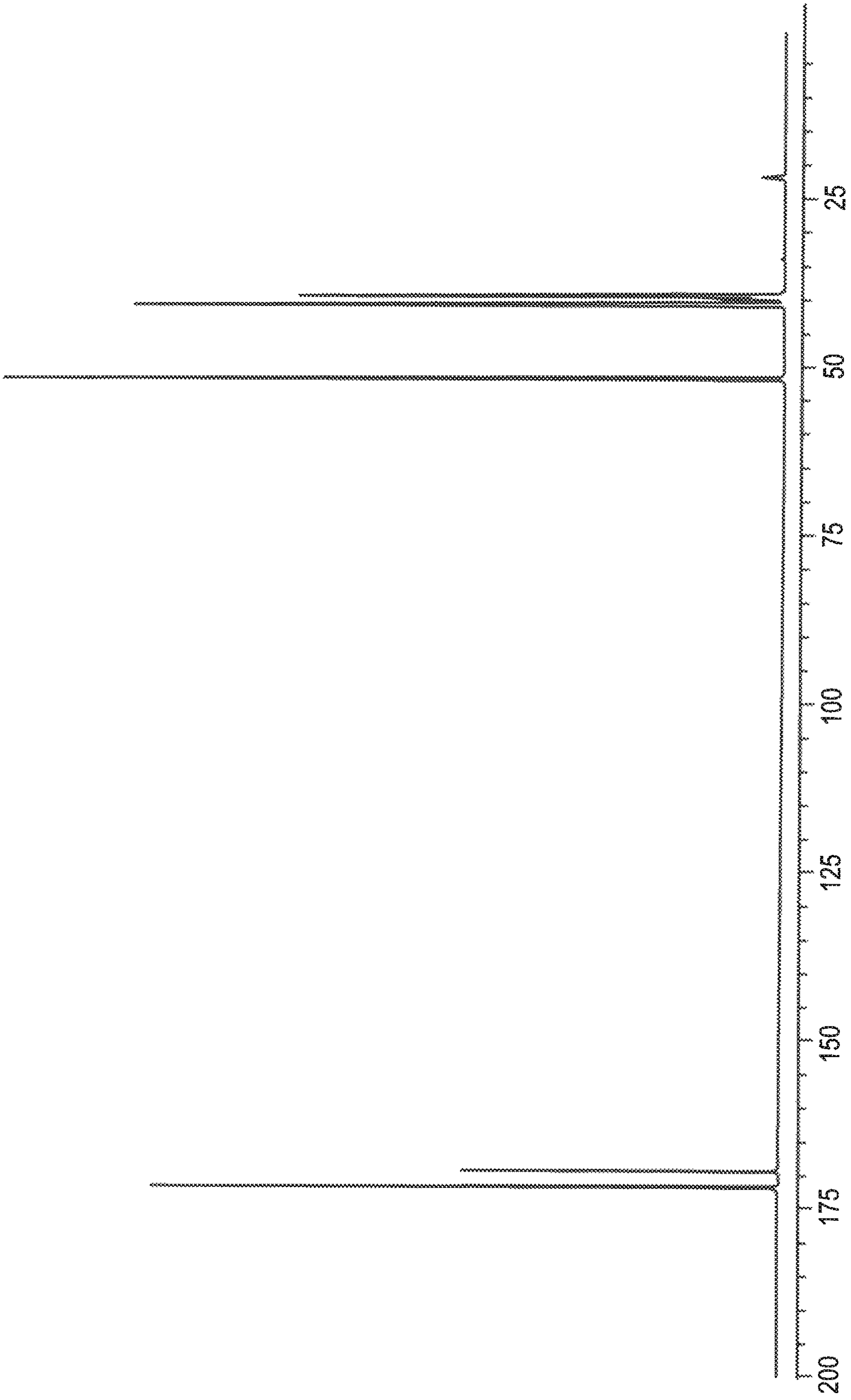
FIG. 12 is a Carbon-13 NMR Spectrum of diNACA-$d_6$.

FIG. 12 is a Carbon-13 NMR Spectrum of diNACA-$d_6$.

Figure 13:
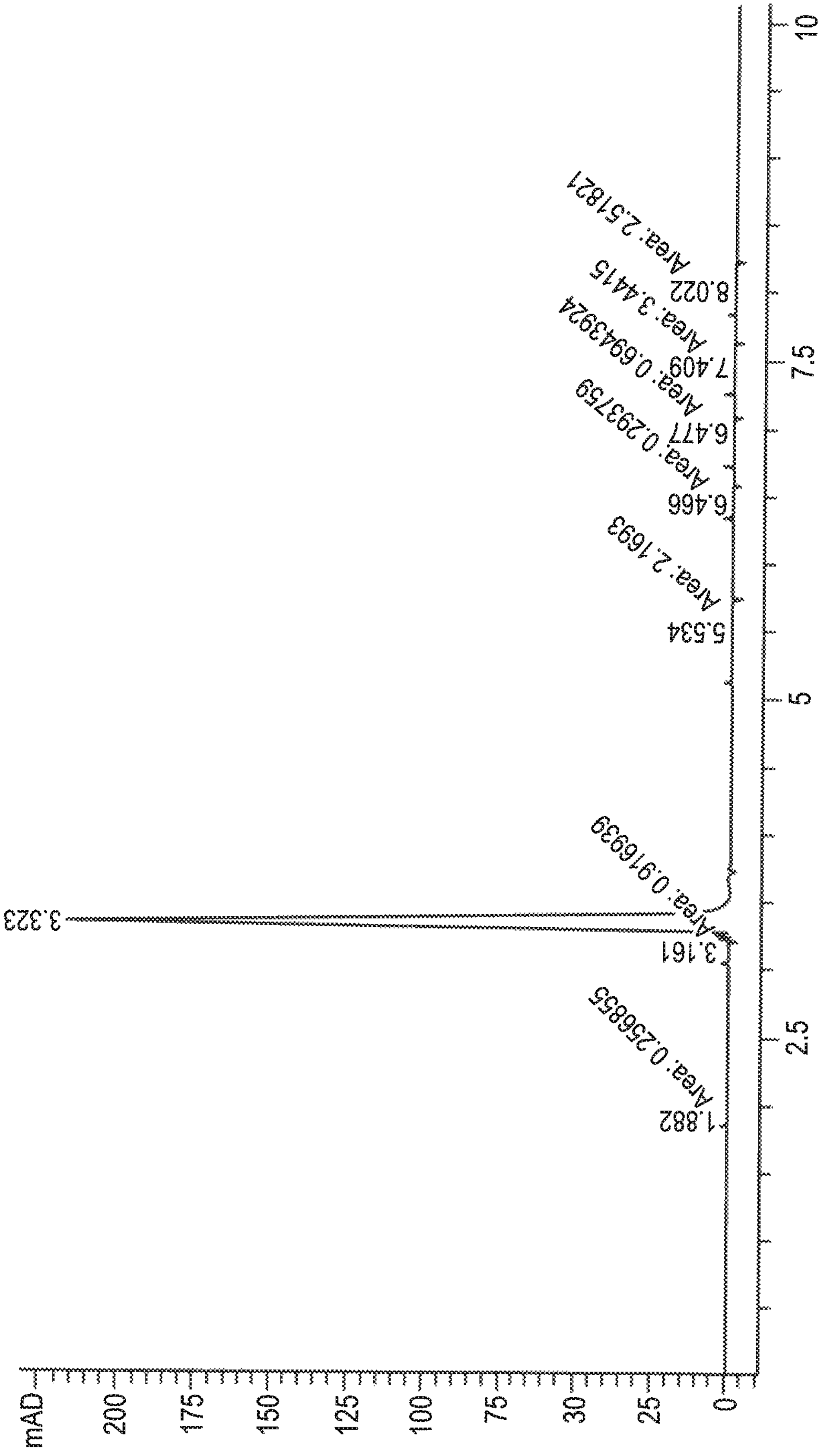
FIG. 13 is an HPLC Chromatogram of diNACA-$d_6$.

FIG. 13 is an HPLC Chromatogram of diNACA-$d_6$.

Figure 14:
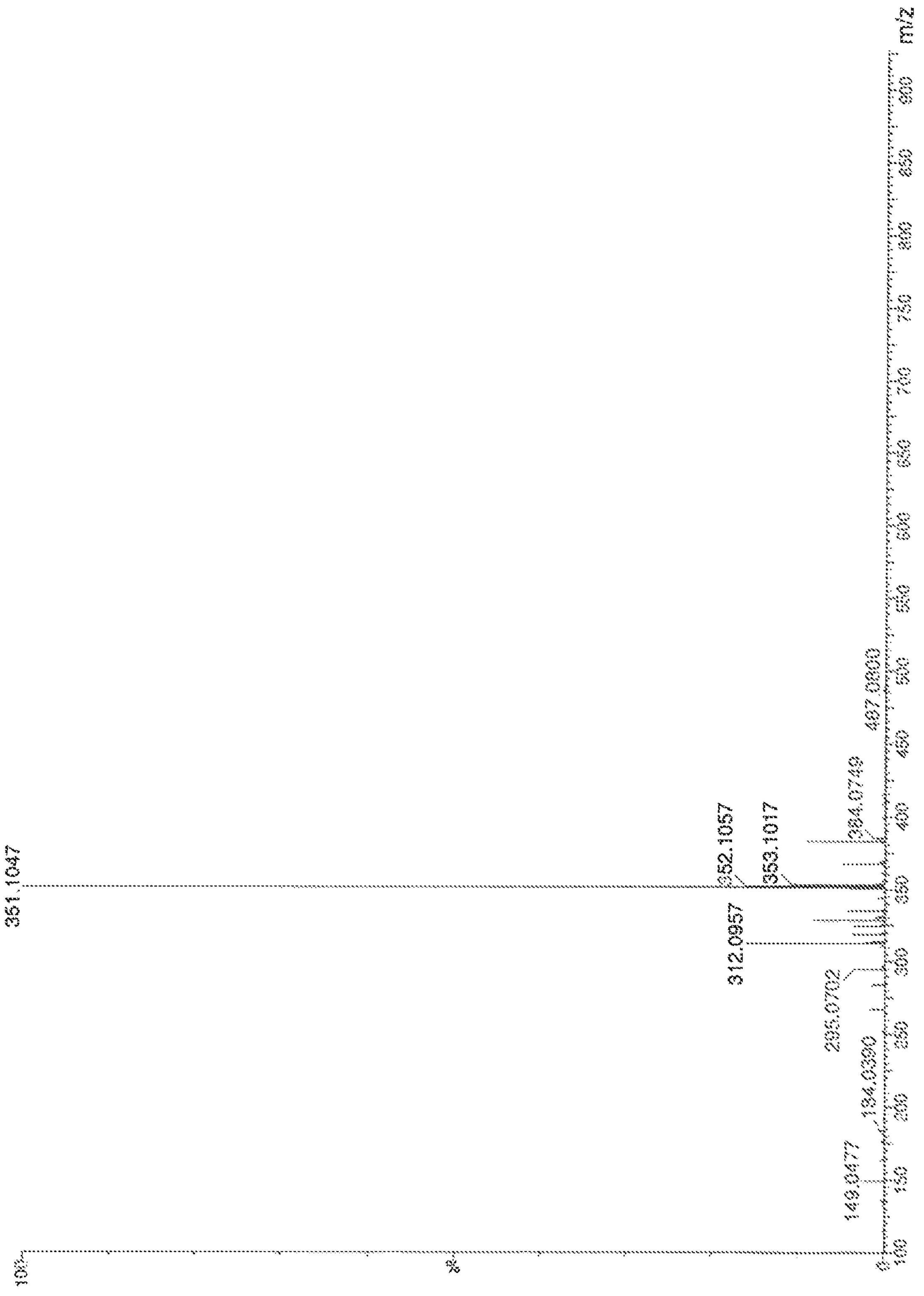
FIG. 14 is a high-resolution Mass Spectrum of diNACA-de: Found m/z 351.1047. $C_{10}H_{12}D_6N_4O_4S_2Na$ [M+Na]+ requires m/z 351.1044. The deviation of 0.9 ppm is within normally accepted limits for the establishment of identity by HRMS. No signal for do material was seen (detection limit about 0.5%).

FIG. 14 is a high-resolution Mass Spectrum of diNACA-do: Found m/z 351.1047. $C_{10}H_{12}D_6N_4O_4S_2Na$ [M+Na]+ requires m/z 351.1044. The deviation of 0.9 ppm is within normally accepted limits for the establishment of identity by HRMS. No signal for do material was seen (detection limit about 0.5%).

Compounds described herein can be provided in isolated or purified form. Isolated or purified compounds are a group of compounds that have been separated from their environment, such as from a crude reaction mixture if made in a laboratory setting or removed from their natural environment if naturally occurring. Examples of the purity of the isolated compound include, for example, at least 50%, 55%, 60%, 65%, 70%, 75%, 80%, 85%, 90%, 95%, 96%, 97%, 98%, 99%, or 100% by weight.

Another aspect of the invention provides a unit quantum of a deuterium-enriched compound described herein, such as an amount of at least (a) one microgram of a disclosed deuterium-enriched compound, (b) one mg, or (c) one gram. In further embodiments, the quantum is, for example, at least 0.01, 0.02, 0.03, 0.04, 0.05, 0.1, 0.2, 0.3, 0.4, 0.5, or 1 mole of the compound. The present amounts also cover lab-scale (e.g., gram scale including 1, 2, 3, 4, 5 g, etc.), kilo-lab scale (e.g., kilogram scale including 1, 2, 3, 4, 5 kg, etc.), and industrial or commercial scale (e.g., multi-kilogram or above scale including 100, 200, 300, 400, 500 kg, etc.) quantities as these will be more useful in the actual manufacture of a pharmaceutical. Industrial/commercial scale refers to the amount of product that would be produced in a batch that was designed for clinical testing, formulation, sale/distribution to the public, etc.

Doses of a compound provided herein, or a pharmaceutically acceptable salt thereof, vary depending on factors such as: specific indication to be treated; age and condition of a patient; and amount of a second active agent used, if any. Generally, a compound provided herein, or a pharmaceutically acceptable salt thereof, may be used in an amount of from about 0.1 mg to about 1 g per day, or from about 0.1 mg to about 500 mg per day, and can be adjusted in a conventional fashion (e.g., the same amount administered each day of the treatment), in cycles (e.g., one week on, one week off), or in an amount that increases or decreases over the course of treatment. In other embodiments, the dose can be from about 1 mg to 1000 mg, from about 1 mg to about 450 mg, from about 0.1 mg to about 150 mg, from about 1 mg to about 300 mg, from about 10 mg to about 100 mg, from about 0.1 mg to about 50 mg, from about 1 mg to about 50 mg, from about 10 mg to about 50 mg, from about 20 mg to about 30 mg, or from about 1 mg to about 20 mg. In yet other embodiments, the daily dose can be from about 50 mg to 75 mg, 75 mg to 100 mg, 100 mg to 125 mg, 125 mg to 150 mg, 150 mg to 175 mg, 175 mg to 200 mg, 200 mg to 225 mg, 225 mg to 250 mg, 250 mg to 275 mg, 275 mg to 300 mg, 300 mg to 325 mg, 325 mg to 350 mg, 350 mg to 375 mg, 375 mg to 400 mg, 400 mg to 425 mg, or 425 mg to 450 mg. In certain embodiments, the diNACA, deuterium-enriched $D_3$-N-acetyl cysteine amide, diNACA-do, or both, is administered at a daily dosage in the range of about 125 mg to 150 mg, 150 mg to 175 mg, 175 mg to 200 mg, 200 mg to 225 mg, 225 mg to 250 mg, 250 mg to 275 mg, or 275 mg to 300 mg. In certain embodiments, the diNACA, deuterium-enriched $D_3$-N-acetyl cysteine amide, diNACA-$d_6$, or both, is administered at a daily dosage in the range of about 50 mg to 75 mg, 75 mg to 100 mg, 100 mg to 125 mg, 125 mg to 150 mg, 150 mg to 175 mg, 175 mg to 200 mg, 200 mg to 225 mg, 225 mg to 250 mg, 250 mg to 275 mg, or 275 mg to 300 mg. In certain embodiments, the diNACA, deuterium-enriched $D_3$-N-acetyl cysteine amide, diNACA-$d_6$, or both, is administered at a daily dosage in the range of about 125 mg to 150 mg or 150 mg to 175 mg. In certain embodiments, the diNACA, deuterium-enriched $D_3$-N-acetyl cysteine amide, diNACA-$d_6$, or both, is administered at a daily dosage in the range of about 125 mg to 175 mg. In certain embodiments, the diNACA, deuterium-enriched $D_3$-N-acetyl cysteine amide, diNACA-$d_6$, or both, is administered at a daily dosage in the range of about 140 mg to 160 mg. In yet other embodiments, the diNACA, $D_3$-N-acetyl cysteine amide, diNACA-$d_6$, or both, is administered at a daily dosage in the range of about 50 mg to 175 mg, or about 125 mg to 175 mg. In yet other embodiments, the daily dose is less than about 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, or 450 mg. In yet other embodiments, the daily dose is less than about 125 mg, 150 mg, or 175 mg. The formulation may also exclude non-active ingredients, in which case the formulation will "consist essentially" of the active agents claimed herein, as non-active ingredients. The formulation may also exclude all other ingredients, in which case the formulation will "consist" of the active agents. Each of these variants are contemplated herein.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112 as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

What is claimed is:

1. A pharmaceutical composition comprising an enantiopure deuterated (2R,2R')-di-N-acetylcysteine amide-$d_6$ (di-NACA-$d_6$), or a physiologically acceptable salt thereof, having a deuterium enrichment above the natural abundance of deuterium.

2. The pharmaceutical composition of claim 1, wherein the deuterated di-N-acetylcysteine amide-$d_6$ has the following formula:

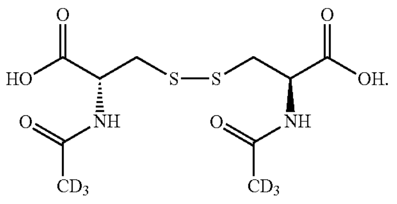 [SMILES: [2H]C([2H])([2H])C(=O)N[C@@H](CSSC[C@H](NC(=O)C([2H])([2H])[2H])C(=O)O)C(=O)O]

3. The pharmaceutical composition of claim 1, wherein the difference in the deuterium enrichment in the $D_3$-positions in the $D_6$-N-acetyl cysteine is about 8 to 10 percentage points compared to a natural abundance of deuterium.

4. The pharmaceutical composition of claim 1, wherein the deuterium enrichment above the natural abundance of deuterium is within a predefined range of 0.02 mol % to 100 mol % deuterium, as determined by NMR spectroscopy in $d_6$-dimethyl sulfoxide using a 500 MHz spectrometer.

* * * * *